US009060935B2

(12) United States Patent
Johnsson et al.

(10) Patent No.: US 9,060,935 B2
(45) Date of Patent: Jun. 23, 2015

(54) PHARMACEUTICAL LIPID COMPOSITIONS

(75) Inventors: Markus Johnsson, Lund (SE); Fredrik Tiberg, Lund (SE)

(73) Assignee: CAMURUS AB (SE)

( * ) Notice: Subject to any disclaimer, the term of this patent is extended or adjusted under 35 U.S.C. 154(b) by 1219 days.

(21) Appl. No.: 11/795,243

(22) PCT Filed: Dec. 9, 2005

(86) PCT No.: PCT/GB2005/004745
§ 371 (c)(1),
(2), (4) Date: May 12, 2008

(87) PCT Pub. No.: WO2006/077362
PCT Pub. Date: Jul. 27, 2006

(65) Prior Publication Data
US 2008/0274176 A1    Nov. 6, 2008

(30) Foreign Application Priority Data

Jan. 21, 2005  (GB) .................................. 0501364.4
Apr. 18, 2005  (GB) .................................. 0507812.6

(51) Int. Cl.
*A61K 9/48* (2006.01)
*A61K 9/127* (2006.01)

(52) U.S. Cl.
CPC ...................................... *A61K 9/127* (2013.01)

(58) Field of Classification Search
None
See application file for complete search history.

(56) References Cited

U.S. PATENT DOCUMENTS

| | | | |
|---|---|---|---|
| 4,938,763 | A | 7/1990 | Dunn et al. |
| 5,340,802 | A | 8/1994 | Shiosaki et al. |
| 5,480,656 | A | 1/1996 | Okada et al. |
| 5,531,925 | A | 7/1996 | Landh et al. |
| 5,639,480 | A | 6/1997 | Bodmer et al. |
| 5,776,885 | A | 7/1998 | Orsolini et al. |
| 5,807,573 | A | 9/1998 | Ljusberg-Wahren et al. |
| 5,955,502 | A | 9/1999 | Hansen et al. |
| 6,066,328 | A | 5/2000 | Ribier et al. |
| 6,113,943 | A | 9/2000 | Okada et al. |
| 6,228,383 | B1 | 5/2001 | Hansen et al. |
| 6,458,924 | B2 | 10/2002 | Knudsen et al. |
| 6,464,987 | B1 | 10/2002 | Fanara et al. |
| 8,097,239 | B2 | 1/2012 | Johnsson et al. |
| 8,182,834 | B2 | 5/2012 | Johnsson et al. |
| 8,187,629 | B2 | 5/2012 | Barauskas et al. |
| 8,236,292 | B2 | 8/2012 | Thuresson et al. |
| 8,236,755 | B2 | 8/2012 | Thuresson et al. |
| 2002/0026027 | A1 | 2/2002 | Ansell |
| 2003/0022242 | A1* | 1/2003 | Anderson ...................... 435/7.1 |
| 2004/0018241 | A1 | 1/2004 | Houze et al. |
| 2004/0201117 | A1 | 10/2004 | Anderson |
| 2005/0136059 | A1 | 6/2005 | Thorpe et al. |
| 2006/0073203 | A1 | 4/2006 | Ljusberg-Wahren et al. |
| 2007/0080323 | A1 | 4/2007 | Joabsson et al. |
| 2007/0110777 | A1 | 5/2007 | Joabsson et al. |
| 2007/0134336 | A1 | 6/2007 | Worle et al. |
| 2007/0231374 | A1 | 10/2007 | Tiberg et al. |
| 2008/0124394 | A1 | 5/2008 | Johnsson et al. |
| 2008/0146490 | A1 | 6/2008 | Joabsson et al. |
| 2008/0161276 | A1 | 7/2008 | Johnsson et al. |
| 2008/0214995 | A1 | 9/2008 | Boyd et al. |
| 2009/0069221 | A1 | 3/2009 | Joabsson et al. |
| 2009/0155193 | A1 | 6/2009 | Joabsson et al. |
| 2009/0170782 | A1 | 7/2009 | Joabsson et al. |
| 2010/0210519 | A1 | 8/2010 | Johnsson et al. |
| 2011/0230569 | A1 | 9/2011 | Nistor et al. |
| 2012/0028890 | A1 | 2/2012 | Nistor et al. |
| 2012/0269772 | A1 | 10/2012 | Thuresson et al. |

FOREIGN PATENT DOCUMENTS

| | | |
|---|---|---|
| EP | 1600162 | 11/2005 |
| WO | 93/06921 A1 | 4/1993 |
| WO | 95/34287 A1 | 12/1995 |
| WO | WO 97/13528 A1 | 4/1997 |
| WO | 98/47487 A1 | 10/1998 |
| WO | 02/02716 A2 | 1/2002 |
| WO | 02/066014 A2 | 8/2002 |
| WO | 02/068561 A2 | 9/2002 |
| WO | 02/068562 A2 | 9/2002 |
| WO | WO 03/002136 A2 | 1/2003 |

(Continued)

OTHER PUBLICATIONS

Kesisoglou, et al., "Liposomal Formulations of Inflammatory Bowel Disease Drugs: Local versus Systemic Drug Delivery in a Rat Model", Pharmaceutical Research, vol. 22, No. 8, Aug. 2005, pp. 1320-1329.

Kamo, et al., "Nonlamellar Liquid Crystalline Phases and Their Particle Formation in the Egg Yolk Phosphatidylcholine/Diolein System", Langmuir, vol. 19, pp. 9191-9195, Published on Web Oct. 1, 2003.

Barauskas et al., Pharmaceutical Nanotechnology, "Interactions of lipid-based liquid crystalline nanoparticles with model and cell membranes", International Journal of Pharmaceutics 391 (2010) pp. 284-291.

(Continued)

Primary Examiner — Snigdha Maewall
(74) Attorney, Agent, or Firm — J.A. Lindeman & Co., PLLC

(57) ABSTRACT

The present invention relates to a particulate composition containing; a) 5 to 90% of at least one phosphatidyl choline component b) 5 to 90% of at least one diacyl glycerol component, at least one tocopherol, or mixtures thereof, and c) 1 to 40% of at least one non-ionic stabilizing amphiphile, where all parts are by weight relative to the sum of the weights of a+b+c and where the composition contains particles of at least one non-lamellar phase structure or forms particles of at least one non-lamellar phase structure when contacted with an aqueous fluid. The invention additionally relates to pharmaceutical formulations containing such compositions, methods for their formation and methods of treatment comprising their administration.

24 Claims, 8 Drawing Sheets

(56) References Cited

FOREIGN PATENT DOCUMENTS

| WO | WO 03/057235 A2 | 7/2003 |
| WO | WO 2004/087215 A1 | 10/2004 |
| WO | 2005/014162 A1 | 2/2005 |
| WO | WO 2005/021022 A2 | 3/2005 |
| WO | WO 2005/046642 A1 | 5/2005 |
| WO | WO 2005/048952 A2 | 6/2005 |
| WO | WO 2005/063213 A1 | 7/2005 |
| WO | WO 2005/070394 A2 | 8/2005 |
| WO | WO 2005/117830 A1 | 12/2005 |
| WO | WO 2006/075123 A1 | 7/2006 |
| WO | WO 2006/075124 A1 | 7/2006 |
| WO | WO 2006/075125 A1 | 7/2006 |
| WO | WO 2006/077362 A1 | 7/2006 |
| WO | WO 2006/131730 A1 | 12/2006 |
| WO | WO 2008/152401 A1 | 12/2008 |
| WO | WO 2009/024795 A1 | 2/2009 |
| WO | WO 2009/024797 A1 | 2/2009 |
| WO | WO 2010/020794 A1 | 2/2010 |

OTHER PUBLICATIONS

Johnsson et al., "Physicochemical and Drug Delivery Aspects of Lipid-Based Liquid Crystalline Nanoparticles: A Case Study of Intravenously Administered Propofol", Journal of Nanoscience and Nanotechnology, vol. 6, No. 9/10, pp. 3017-3024, 2006.
Tiberg et al., "Dred delivery applications of non-lamellar liquid crystalline phases and nanoparticles", J. Drug Del. Sci. Tech., 21 (1) pp. 101-109, 2011.
Invitrogen, "Pluronic F-127", Molecular Probes Invitrogen Detection Technologies, pp. 1-2, 2008.
Office Action in U.S. Appl. No. 11/795,249 dated Dec. 4, 2013.
Office Action in U.S. Appl. No. 11/795,250 dated Dec. 4, 2013.
Office Action in U.S. Appl. No. 12/664,835 dated Oct. 25, 2013.
About Sandostatin: Proven Control of GH, 1GF-1 and Gastrointestinal Hormone, from www.sandostatin.com/about.sandostatin/index.html and linked documents.
"Acromegaly" from www.niddk.nil.gov/health/endo/pubs/acro/acro.htm.
American Peptide Company, Product Details "Somatostatin and analogs," from www.americanpeptide.com/.
N. Ardjomand et al., "Expression of Somatostatin Receptors in uveal melanomas," Inv. Opthalmol. & Vis. Sci., 2003, vol. 44, No. 3, pp. 980-987.
R. Berges, "Eligard: Pharmacokinetics, Effect on Testosterone and PSA Levels and Tolerability," European Urology Supplements, 2005, vol. 4, pp. 20-25.
Chang, J., "Use of GnRH agonists in the treatment of hyperandrogenism and hirsutism," print out from http://patients.uptodate.com.
P. Chanson et al., "Comparison of octreotide acetate LAR and lanreptide SR in patients with acromegaly," Clin. Endocrinology, 2001, vol. 54, No. 1, pp. 11-13, (Abstract only).
Comets et al., "Non parametric analysis of the absorption profile of octreotide in rabbits from long-acting release formulation OncoLAR," J. Controlled Release 59:197-205 (1999).
F. Dall'Antonia, "Structure determination of organo-silicon compounds.", pp. 6 to 8 from http://shelx.un-iac.gwdg.de/-fabio/endwkcon.htm.
Definition of analog from http://cancerweb.ncl.ac.uk!omd/about.html, pp. 1-5. Accessed Jul. 7, 2005.
B. L. Erstad, "Octreotide for acute variceal bleeding," Ann. Pharmacother., 2001, vol. 35, No. 5, pp. 618-626. (Abstract only).
FDA's 510(k) Summary of Camurus AB, episil® K101769.
A. K. Flogstad et al., "Sandostatin LAR in acromegalic patients: long term treatment," J. Clinical Endocrinology & Metabolism, 1997, vol. 82, No. 1, pp. 23-28.
P. R. Gibson & J. G. Muir, "Reinforcing the mucus: a new therapeutic approach for ulcerative colitis," Gut, 2005, vol. 54, pp. 900-903.
L. M. Grant & F. Tibert, "Normal and Lateral Forces between Lipid Covered Solids in Solution: Correlation with Layer Packing and Structure," Biophysical Journal, 2002, vol. 82, pp. 1373-1385.
B.A. Hills, "Surface-active phospholipid: a Pandora's box of clinical applications. Part II. Barrier and lubricating properties," Internal Medicine Journal, 2002, vol. 32, pp. 242-251.
G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.
H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.
Indications and Usage of Eligard, pp. 1-5, print out from http:ffwww.rxlist.com.
Information About Buprenorphine Therapy, print out from http://buprenorphine.samhsa.gov/about.html, pp. 1-4.
Information on Goserelin Acetate print out form http://www.bachem.com/.
Information on Goserelin Subcutaneous, Monograph—Goserelin Acetate, pp. 1-7, print out form www.medscape.com.
Information on Leuprolide Intramuscular, Monograph—Leuprolide Acetate, pp. 1-20, print out for www.medscape.com.
Information on Leuprolide (3 Month) Intramuscular, Monograph—Leuprolide Acetate, pp. 1-20, print out from www.medscape .com.
J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).
L. M. Knudsen, "Glucagon-like Peptide-1: The Basis of a New Class of Treatment for Type 2 Diabetes," J. Med. Chem. (2004), vol. 47, pp. 4128-4134.
L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.
I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.
"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.
Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.
Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.
Martel et al., "Enzyme Linked !mmunosorbent Assay (EUSA) Method for the Determination of TH0318, a New GLP-1 Analogue in Development for Diabetes," Poster.
MSDS for Ethylene Glycol and Abbreviations used in Toxicity data.
Novartis Pharmaceuticals Corporation, "Sansdostatin LAR Depot (octreotide acetate for injectable suspension)", pp. 1-19.
PDR Information on Eligard 30 mg (Sanofi-Synthelabo), print out from www.Drugs.com, pp. 1-14.
Pharmaceutical Information on Lupron Depot, print out from www.rxmed.com, pp. 1-8.
Product Information on Zoladex Goserelin Acetate Implant (Equivalent to 10.8 mg goserelin).
Product Specification of Leuprolide by GL Biochem, print out from http://www.glschina.com.
Published Data Provided by Sandostatin LAR "The Latest Research and Treatment Information for Pituitary Disorders" from http://www.sandostatin.com/published data/index.html.
O. Sartor "Eligard: Leuprolide Acetate in a Novel Sustained-Release Delivery System," Urology, 2003, vol. 61, (Supplement 2A), pp. 25-31.
K. J. Schuh et al., "Onset, magnitude and duration of opioid blockade produced by buprenorphine and naltrexone in humans," Psychopharmacology, (Ber1), Jul. 1999, vol. 145, No. 2, pp. 162-174 (Abstract only).

(56) References Cited

OTHER PUBLICATIONS

J. C. Shah et al., "Cubic phase gels as drug delivery systems," Advanced Drug Delivery Reviews, 2001, vol. 47, pp. 229-250.
"Setting new standards of care," Mixing and Administration instructions for Sandostatin LAR.
W. Stremmel et al., "Retarded release phosphatidylcholine benefits patients with chronic active ulcerative colitis," Gut, 2005, vol. 54, pp. 966-971.
A Sturm & A. U. Dignass, "Modulation of gastrointestinal wound repair and inflammation by phospholipids," Biochimica et Biophysica Acta, 2002, vol. 1582, pp. 282-288.
Svanberg et al., "A New Preventive Strategy Using a Bioadhesive Oromucosal Lipid Solution and Oral Cryotherapy to Protect the Oral Cavity—and Reduce the Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).
Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).
Treating Acromegaly, from http://www.sandostatin.com/Ireating acromegaly/index.html and linked documents.
Welin et al., "High-dose treatment with a long-acting somatostatin analogue in patients with advanced midgut carcinoid tumours," 2004, Society of the European Journal of Endocrinology, vol. 151, pp. 107-112.
Wermuth, Pure and Appl. Chem, 1998, 70, 1129-1143.
E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).
E. A. Woltering, "A discussion on the utility of various routes of administration of octreotide acetate," from http://www.carcinoid.org/medpro/docs/WoltPump2005.htm.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.
International Preliminary Report on Patentability of PCT/GB2008/002035 Dec. 17, 2009.
Written Opinion of PCT/GB2008/002035 dated Oct. 6, 2008.
International Search Report of PCT/GB2008/002857 dated Jan. 28, 2009.
International Preliminary Report on Patentability and Written Opinion of PCT/GB2008/002857 dated Feb. 24, 2010.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,249 dated Jul. 19, 2011.
Office Action in U.S. Appl. No. 11/795,249 dated Oct. 25, 2010.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/908,740 dated Feb. 14, 2012.
Office Action in U.S. Appl. No. 11/877,935 dated Dec. 21, 2010.

* cited by examiner

PHARMACEUTICAL LIPID COMPOSITIONS

This application claim priority to PCT Application No. PCT/GB2005/004745, filed Dec. 9, 2005, which claims priority to GB 0501364.4, filed Jan. 1, 2005 and GB 0507812.6, filed Apr. 18, 2005, all of which are herein incorporated by reference in their entirety.

The present invention relates to the protection, solubilisation, stabilisation and delivery of active agents in pharmaceutical and neutraceutical compositions. In particular, the invention relates to amphiphilic compositions and formulations, and active agent delivery systems based upon these.

Amphiphile-based formulations show considerable potential in the delivery of many substances, especially for in vivo delivery to the human or animal body. Because the amphiphile has both polar and apolar groups which cluster to form polar and apolar regions, it can effectively solubilise both polar and apolar compounds. In addition, many of the structures formed by amphiphiles/structuring agents in polar and/or apolar solvents have a very considerable area of polar/apolar boundary at which other amphiphilic compounds can be adsorbed and stabilised.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ "sponge" phase which comprises a multiply interconnected three-dimensional bi-continuous network of bilayer sheets which lack the long-range order of the liquid crystalline phases. Depending upon their curvature, these phases may be described as normal (mean curvature towards the apolar region) or reversed (mean curvature towards the polar region). Where the spontaneous curvature of the lipid system is close to zero, the structures are typically lamellar, such as uni- or multi-lamellar vesicles/liposomes and where the spontaneous curvature is more negative or positive, micellar, cubic and hexagonal phases typically dominate.

The non-lamellar (e.g. liquid crystalline and $L_3$) phases are thermodynamically stable systems. That is to say, they are not simply a meta-stable state that will separate and/or reform into layers, lamellar phases or the like, but are the thermodynamically stable form of the mixture.

Both lamellar and non-lamellar systems have been investigated for their properties as carriers and/or excipients for dietary, cosmetic, nutritional, diagnostic and pharmaceutical agents but the non-lamellar systems are thought to have considerable advantages in terms of their high internal surface area between polar and apolar regions. This has led to considerable investigation of non-lamellar phases particularly in controlled-release formulations and for solubilising compounds of relatively low solubility.

As discussed above, a bulk non-lamellar phase is typically a thermodynamically stable system. In addition, this bulk phase may be dispersed in a polar or non-polar solvent to form particles of a non-lamellar (especially liquid crystalline) phase in a bulk solvent. This allows the advantages of bulk non-lamellar phases to be applied in situations where use of a bulk non-miscible phase would cause problems, such as in parenteral applications. Further control of a compound's release profile may also be achieved by such a dispersion of non-lamellar particles.

Liquid crystalline or $L_3$ phase can be in or near thermodynamic equilibrium with the excess solvent and may be dispersed into colloidally stable dispersions of non-lamellar particles. Such particles may be fully (i.e. thermodynamically) stable, or may gradually degrade, thereby providing control over the release profile for active agents formulated therewith. The formation of dispersions can be spontaneous or as the result of mechanical force such as shearing or ultrasound. These non-lamellar particles are of considerable interest in the delivery of active agents and have been proposed as carriers for many such actives.

A method for the formation of dispersed particles of non-lamellar phase in solvents such as water is described in U.S. Pat. No. 5,531,925. Such particles have a non-lamellar liquid crystalline or $L_3$ interior phase and a lamellar or $L_3$ surface phase and may also contain active ingredients.

Known particles of liquid crystalline or $L_3$ interior phase may be formed by methods such as adding to this phase a solution of surface-phase forming agent, stirring to form a coarse dispersion and fragmenting the resulting mixture.

In order to assess the presence of a liquid crystalline phase, the prospective liquid crystalline material may be examined by use of small-angle X-ray diffraction (SAX), cryo-Transmission Electron Microscopy (cryo-TEM) or Nuclear Magnetic Resonance (NMR) spectroscopy studies. The sizes and size distributions of the dispersed particles may be examined by light scattering, particularly by use of laser light scattering instruments.

Dispersions containing active ingredients and particularly those for intravenous administration to the human or animal body are desirably colloidal, that is they should be of a particle size no greater than 10 µm, especially no greater than 5 µm and particularly no greater than 1 µm. If particles within the dispersion exceed this size then the dispersion may not be colloidally stable and there is a considerable risk of causing embolism when the preparation is administered intravenously. Furthermore, it is desirable that the distribution of particle sizes be narrow to maximise control over the release of any active agent. Where a particulate composition is to be administered by a method other than intravenously (e.g. orally, intramuscularly, subcutaneously, rectally or by inhalation), then the particles need not necessarily be colloidal but it remains advantageous to provide a well characterised and reproducible particle size distribution in order to control the rate of decomposition of the particles and/or release of the active agents.

The particle size of a particulate composition should also be stable to storage over a considerable period of time. If the distribution of particle sizes changes significantly then the effective transport rate for composition (e.g. due to diffusion and rate of release of any active agent) may be adversely affected. Of still greater concern is the stability of particle sizes in a colloidal dispersion for intravenous administration. If the particle size distribution of such a dispersion is not stable (e.g. to storage and distribution) then large particles may form over time and be dangerous when administered. Even if not directly dangerous, storage instability can cause significant variability in pharmacokinetics, dynamics and/or efficacy.

In addition to control over particle size, it is desirable to maximise the proportion of particles which are in the desired, non-lamellar, phase in order to maximise the beneficial effects of this in terms of loading capacity, protective encapsulation, controlled release, reproducibility, etc. The proportion of lamellar particles such as uni- or multi-lamellar vesicles should therefore be minimised.

Known methods for the formation of dispersed particles of non-lamellar phase are highly effective, but typically produce a relatively broad distribution of particle sizes and a considerable proportion of "contaminant" lamellar vesicular particles. Increasing the proportion of fragmenting and/or stabilising agent (e.g. surfactant, copolymer and/or protein) in the formulation or increasing the energy input of the homogenisation process may be used to narrow the particle size distribution but at the expense of increasing the proportion of lamellar particles.

One limitation of non-lamellar compositions presently available or suggested is that they frequently rely upon lipids which are not well tolerated in vivo at elevated concentrations. In particular, commonly used monoacyl glycerols (including the popular glyceryl monooleate—GMO) can be toxic if administered (especially parenterally) at high concentrations, which can be dose-limiting. The possibility of toxic side effects from the lipid carrier can also limit the range of indications for which an active agent is used to those of a highly serous nature, where the risk of side-effects may be tolerated. It would, therefore, be a considerable advance to provide lipid compositions which were formable and stable as particulate dispersions, showed predictable non-lamellar phase behaviour and had decreased toxicity, (e.g. as seen from haemolysis indices and/or acute toxicity studies) when compared with widely used compositions (e.g. those including GMO). It would be of further advantage if such formulations were formable and stable as colloidal sized particles (e.g. 0.05 to approximately 2 μm diameter) and had a narrow, mono-modal, particle size distribution. It has been observed in the literature that stable particular dispersions are particularly difficult to provide and that only lamellar dispersions are stable to storage for more than a few days (Kamo et al. *Langmuir* 19, 9191-9195 (2003)).

The present inventors have unexpectedly established that a mixture of at least 3 amphiphilic components comprising a diacyl glycerol (DAG), a tocopherol, or a diacyl phosphatidyl ethanolamine (PE) component, or mixtures thereof, a phosphatidyl choline (PC) component and a non-ionic stabilising component is highly effective in forming stable non-lamellar dispersions and can show surprisingly low toxicity in vivo.

In a first aspect, the present invention therefore provides a particulate composition comprising:
  a) 5 to 90% of at least one phosphatidyl choline component,
  b) 5 to 90% of at least one diacyl glycerol component, at least one tocopherol, or mixtures thereof and
  c) 1 to 40% (preferably 2-40%) of at least one non-ionic stabilising amphiphile,
wherein all parts are by weight relative to the sum of the weights of a+b+c and wherein the composition comprises particles of at least one non-lamellar phase structure or forms particles of at least one non-lamellar phase structure when contacted with an aqueous fluid.

Preferred compositions of the present invention additionally contain at least one active agent as described herein and may contain a solvent (particularly water or an aqueous solvent or solvent mixture). The compositions may also contain suitable carriers, excipients, fillers, stabilisers and similar components.

In a further aspect, the present invention provides a pharmaceutical formulation comprising at least one composition of the invention and at least one pharmaceutically tolerable carrier or excipient.

In a further aspect, the present invention provides a method for the treatment of a human or animal subject comprising administration of a composition of the present invention, optionally including an active agent. In this aspect, the method of treatment is in particular a method for the treatment of inflammation and/or irritation, especially in a body cavity such as the gastrointestinal tract.

In a still further aspect, the present invention provides for the use of a composition of the present invention in therapy, and in particularly for the use of a composition of the present invention, optionally including an active agent, in the manufacture of a medicament for the treatment of inflammation and/or irritation, especially in a body cavity such as the gastrointestinal tract.

The ternary amphiphilic compositions of the invention comprise at least one PC component (component a), at least one DAG, at least one tocopherol, and/or at least one PE component (component b) and at least one non-ionic stabilising amphiphilic component (component c). Component c will, in particular facilitate fragmentation of the composition.

At least 5% by weight of total amphiphilic components (a+b+c) should be component a. Preferably this will be 5 to 50% and more preferably 10 to 40%. Correspondingly, component b should be at least 5% by weight of a+b+c, preferably 20 to 85%, more preferably 30 to 75%. Component c should be present at 2 to 40%, preferably 3 to 35% and more preferably 5 to 30% of the total weight of a+b+c.

In the ternary amphiphilic compositions, the phosphatidyl choline component "a" consists predominantly of lipids having the phosphatidyl choline polar group with two non-polar acyl chains attached by ester linkages. This component is referred to herein, as in the literature, as phosphatidyl choline (PC) and may consist of one pure compound, such as synthetic dioleoyl phosphatidyl choline or, more preferably, will be a mixture of PCs such as that derived from a purified natural source. PC is a particularly advantageous component in that it is widely and readily available and can conveniently be purified from a variety of natural sources. The ability of the present invention to function effectively with naturally derived products, including mixed PCs, is a considerable advantage over certain other lipid components, such as dioleoyl phosphatidyl ethanolamine (DOPE) which are much more complex to extract & purify or must be synthesised, which makes them much more difficult to produce and obtain on an industrial scale.

Typically, PCs extracted from natural sources will have a mixture of acyl chains and this mixture will vary somewhat depending upon the tissue from which the extract was taken. Liver PC, for example has a relatively wide range of acyl chain lengths (at least $C_{16}$ to $C_{20}$) and has significant proportions of acyl groups which are saturated and which have more than 2 unsaturations. In contrast, Soy PC typically contains largely $C_{16}$ to $C_{18}$ acyl groups with zero or two unsaturations. This allows the behaviour of the compositions of the present invention to be subtly altered by selecting an appropriate PC component or mixtures thereof. Preferred PCs include Egg, Heart, Brain, Liver and particularly Soy PC (SPC). The PC or any portion thereof may also be hydrogenated where a higher proportion of saturated PCs is desired.

Since the PC component of the present invention is preferably a natural extract, it is common for a small amount of non-PC "contaminant" to be present. The exact level of purity of the PC component in terms of content of lipids having other polar groups will depend upon the particular application for which the compositions of the invention are to be used. The important factor is that the phase behaviour, remarkably high stability and remarkably low toxicity of the compositions should be maintained by choice of suitably pure components. So long as this remains acceptable then the purity of the PC will be of relatively minor significance. As a general guide, however, the PC component will commonly contain no more than 10% by weight of lipids with non-PC polar groups. In some embodiments this will preferably be no more than 5% and more preferably no more than 2% by weight.

In the compositions of the invention, component b) is a diacyl glycerol (DAG), and/or a tocopherol. These may consist of a single, pure diacyl glycerol, or tocopherol, may be a mixture of diacyl glycerols, and/or tocopherols, or may be a purified natural extract with a high diacyl glycerol, and/or tocopherol content. Preferred diacyl glycerols have acyl groups independently having 10 to 24 carbons, preferably 12 to 20 carbons, and most preferably 14 to 18 carbons. Saturated and/or unsaturated acyl groups are suitable but groups with one, two or three double bonds are preferred. The acyl groups may be the same or different. A highly preferred DAG is glycerol dioleate (GDO) and mixtures thereof.

As used herein, the term "a tocopherol" is used to indicate the non-ionic lipid tocopherol, often known as vitamin E, and/or any suitable salts and/or analogues thereof. Suitable analogues will be those providing the phase-behaviour, stability and lack of toxicity which characterises the compositions of the present invention and will generally not form liquid crystalline phase structures as a pure compound in water. The most preferred of the tocopherols is tocopherol itself, having the structure below. Evidently, particularly where this is purified from a natural source, there may be a small proportion of non-tocopherol "contaminant" but this will not be sufficient to alter the advantageous phase-behaviour, stability and lack of toxicity. Typically, a tocopherol will contain no more than 10% of non-tocopherol-analogue compounds, preferably no more than 5% and most preferably no more than 2% by weight.

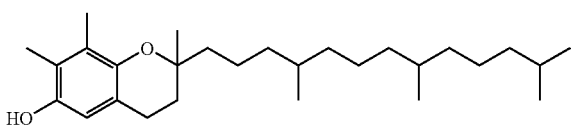

Tocopherol

As with the PC component, component b, for example diacylglycerol, and/or tocopherol, may be provided as a natural extract. This has significant advantages in terms of availability and reliability of the materials. Where a DAG component is a natural extract, however, it is likely that a small amount of non-DAG lipid will remain present. As with the PC component, the crucial test of purity for the DAG component will be that the composition provides the advantageous stability and non-toxicity of the present invention. Typically the DAG component will have no more than 15% by weight of other lipids, preferably no more than 10% and more preferably no more than 5%. DAGs (as described herein) are preferred component b)s.

A preferred combination of constituents for component b) is a mixture of at least one DAG (e.g. GDO) with at least one tocopherol. Such mixtures include 2:98 to 98:2 by weight tocopherol:GDO, e.g. 10:90 to 90:10 tocopherol:GDO and especially 20:80 to 80:20 of these compounds.

A highly preferred combination of components a and b is PC with DAG, wherein both components have at least 50% C18:1 (oleoyl) and/or 50% C18:2 (linoleoyl) acyl groups. Soy PC and Egg PC are particularly preferred Examples. A preferred a weight ratio for these is between 1:5 and 3:2, most preferably 2:5 to 4:5 PC:GDO. One measure of the biological activity of a lipid is its solubility in water or aqueous solutions. Components with relatively high aqueous solubilities maintain a higher equilibrium concentration of dissolved lipid monomer in solution and this can be at least partially responsible for the observed biological effects. The commonly used "glycerol monooleate" (GMO), for example, has an equilibrium water solubility of the order of $10^{-7}$ M at room temperature and greater at physiological temperature. In contrast, preferred diacyl glycerols and diacyl phosphatidyl ethanolamines may have a solubility of no more than $10^{-8}$ or more typically $10^{-9}$ M at room temperature, preferably $5 \times 10^{-10}$ M and more preferably $10^{-10}$ M or less. The minimum desirable solubility is generally around $10^{-15}$ M. In particular, at high dilution, the stability of the non-lamellar system will depend upon the rate at which lipid molecules leave the surface of the structured material and diffuse into solution. The stability of a dispersion of non-lamellar particles will thus be directly related to the solubility of the monomer in the solvent.

Component c acts as a fragmentation agent and helps both in the control and stability of particle phase behaviour and in encouraging and stabilising the fragmentation of the non-lamellar phase into particles. Component c will be present at a level sufficient to bring about the fragmentation of the composition and/or to stabilise the fragmented non-lamellar phase particles. Such fragmentation may be spontaneous or may require physical fragmentation such as by shearing and/or ultrasonication. The skilled worker will have no difficulty in assessing whether any composition contains sufficient fragmentation agent in view of the Examples herein.

The non-ionic stabilising amphiphile "c" is, in general, a component which improves the stability of the dispersion, particularly as colloidal particles. The preferred form of these non-ionic amphiphiles is a non-ionic lipid grafted with a polyoxyethylene and/or polyoxypropylene chain (or a copolymer thereof).

Such compounds are, for example, polyoxyalkyl grafted fatty acids, or substituted fatty acids (especially hydroxylated fatty acids), polyoxylalky grafted lipids or polyols having polyoxyalkyl groups grafted to one or more (preferably all) alcohol moieties and having one or more fatty acid chains joined to the opposite end of one or more of the polyoxyalkyl chain. Examples include polyethylene glycol (PEG) sterate, PEG disterate, PEG laurate, PEG oleate, polyethoxylated caster oil, PEG-DOPE, PEG-(4-hydroxy sterate) (Solutol), PEG-sorbitan-monolaurate (Polysorbate 20 or 21), PEG-sorbitan-monopalmitateate (Polysorbate 40), PEG-sorbitan-monosterate (Polysorbate 60 or 61), PEG-sorbitan-tristerate (Polysorbate 65), PEG-sorbitan-monooleate (Polysorbate 80 or 81), PEG-sorbitan-trioleate (Polysorbate 85), PEG-sorbi-tan-monoisooleate (Polysorbate 120) and d-alpha tocopheryl polyethylene glycol 1000 succinate (Vitamin E TPGS). PEG chains may be attached to the other components of the amphiphile by ester or ether bonds as appropriate. Typically, the total polyoxyalkylene content of a molecule of component c will be no more than 50 monomers, preferably no more than 30 monomers. Most preferred are Polysorbates 20 and 80, solutol, d-alpha tocopheryl polyethylene glycol 1000 succinate (Vitamin E TPGS) and polyethoxylated caster oil.

The present inventors have now established that the stability of the non-lamellar particulate dispersions shows considerable dependence on the type of stabilising agent used. In particular, the dispersing agents indicated above are highly preferred because it has been found that high molecular weight surfactants are notably less stabilising to the particulate dispersion than the lower molecular weight compounds indicated. In one embodiment, therefore, component c) should comprise or preferably consist essentially of, or consist of surfactants with a molecular weight below 10,000 amu, preferably below 8,000 and more preferably below 5000 amu. Similarly, component c should preferably not contain a block-copolymer surfactant, especially one with molecular weight above the ranges indicated above. This is particularly surprising because higher molecular weight surfactants have been shown as effective for stabilising related compositions in lamellar form.

One important aspect of the present invention is that the compositions may be formulated as preconcentrates, containing a cosolvent, as discussed herein. These preconcentrates are particularly suitable for use as controlled release system in parenteral applications. In this use, the most useful ratios between c/a+b+c are 1-30% of component c, more preferably 3-25%. For compositions forming depots intended for release over around one week, the most preferred range is 3-10% c.

The amphiphile components of the compositions of the invention may consist essentially of, or consist of, components a), b) and c) only (plus any active if this is amphiphilic). In this embodiment at least 95%, preferably at least 98% and most preferably substantially 100% of the amphiphile components will be one of these. Alternatively, an additional, optional, amphiphilic component d) may be present in amounts up to 10% by weight of a)+b)+c)+d), preferably up to 8%, more preferably up to 5%. This component d) may be any suitable amphiphile, such as a natural or synthetic lipid or a derivative or analogue thereof. A highly preferred component d) is an ionic lipid, such as a fatty acid or biotolerable salt thereof.

The compositions of the present invention comprise non-lamellar particles or are compositions which form such particles on contact with an aqueous fluid. Such a fluid may be a fluid for delivery to a subject (e.g. water or sterile saline) or may be a body fluid, particularly gastric fluid, intestinal fluid, fluid at mucosal surfaces, blood or intercellular fluid.

As use herein, the term "non-lamellar" is used to indicate a cubic, hexagonal, $L_2$ or $L_3$ phase structure or any combination thereof, as opposed to lamellar structures as found in lamellar phase or liposomes/vesicles. Where a particle is described as having a non-lamellar phase or structure, this indicates that at least the particle interior has this structure. Many of the particles will have two distinct regions, an internal region and a surrounding surface region. The surface region, even in a "non-lamellar" particle may be lamellar or crystalline and may be any phase including highly ordered crystalline layers, liquid crystal phases and virtually orderless fluid layers.

The term "lamellar particles" is used herein to indicate vesicular particles (e.g. liposomes) characterised in that they comprise one or more outer lamellar bilayers of amphiphile, surrounding an inner solvent compartment.

In one aspect of the present invention, the compositions comprise non-lamellar particles. This indicates that of the (preferably colloidal) particles present, at least 50%, preferably at least 75% and most preferably at least 85% (as measured by volume) are non-lamellar (e.g. as judged by laser diffraction combined with cryo-TEM or SAXS). In an alternative aspect of the present invention, the compositions form non-lamellar particles on contact with an aqueous fluid. This indicates that upon contact with an aqueous fluid (as described herein) at least 50%, preferably at least 75% and most preferably at least 85% of the particles (as measured by volume) become non-lamellar particles.

In a preferred embodiment of the present invention, the present compositions comprise or generate particles of reversed hexagonal and/or $L_3$ phase. Most preferably the compositions comprise or generate particles of $L_3$ phase. $L_3$, otherwise known as "sponge" phase lacks the long-range order of a true-liquid crystalline phase but consists of multiply interconnected sheets of lipid bilayer where these "interconnections" do not adopt the regular arrangement seen in cubic liquid crystalline structures.

In an alternative an also highly advantageous embodiment, the compositions of the invention may form $I_2$ or $L_2$ non-lamellar phases. The $I_2$ phase is a reversed cubic liquid crystalline phase having discontinuous aqueous regions. This phase is of particular advantage in the controlled release of active agents and especially in combination with polar active agents, such as water soluble actives. The $L_2$ phase has similar advantages and in a so-called "reversed micellar" phase having a continuous hydrophobic region surrounding discrete polar cores.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which and $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

Where an active agent is formulated in a composition of the invention, the active agent will frequently have an effect upon the phase behaviour of the structuring agent(s). For example, certain active agents (such as cyclosporin A) introduce greater negative curvature than some structuring agents and at high concentrations may cause the formation of highly negatively curved phases, such as the reversed micellar $L_2$ phase rather than a cubic or hexagonal liquid crystalline phase. Nonetheless, such an active agent could be formulated into, for example, a reversed hexagonal phase by formulation with a mixture of components a, b and c having a less negative spontaneous curvature. By this method, the overall mixture provides the appropriate negative curvature to allow use in the compositions of the invention.

The skilled worker will be able to use standard methods to assess the degree of spontaneous curvature of any particular structuring agent (or mixture thereof with other components) or the effect on this by including an active agent. This might be done, for example, by studies of the bulk phase behaviour of each structuring agent in water and subsequent studies with varying concentrations of active agent included. The phases can be examined by any of the methods indicated herein (e.g. polarised light, SAXS, cryo-TEM etc.) and an appropriate blend of components chosen for each case. In some circumstances, where the effect of the active agent on the phase behaviour of the mixture is significant, the structuring agent(s) chosen may not provide the desired non-lamellar phase in themselves (e.g. may have too small or too great spontaneous curvature) but will generate this phase only when also formulated with the active agent. The equilibrium phase may thus change from, for example, cubic to hexagonal liquid crystalline phase upon addition of the active agent.

In one preferred aspect, the compositions of the present invention comprise at least one active agent. Suitable active agents include human and veterinary drugs and vaccines, diagnostic agents, "alternative" active agents such as plant essential oils, extracts or aromas, cosmetic agents, nutrients, dietary supplements etc. Examples of suitable drugs include antibacterial agents such as β-lactams or macrocyclic peptide antibiotics, anti fungal agents such as polyene macrolides (e.g. amphotericin B) or azole antifungals, anticancer and/or anti viral drugs such as nucleoside analogues, paclitaxel, and derivatives thereof, anti inflammatories, such as non-steroidal anti inflammatory drugs, cardiovascular drugs including cholesterol lowering and blood-pressure lowing agents, analgesics, anaesthetics, antidepressants including serotonin uptake inhibitors, vaccines and bone modulators. Diagnostic agents include radionuclide labelled compounds and contrast agents including X-ray, ultrasound and MRI contrast enhancing agents. Nutrients include vitamins, coenzymes, dietary supplements etc. The active agents for use in the present invention will generally not be any of components a, b, or c as described herein. Other preferred active agents include insulin and insulin analogues, growth hormones such as human growth hormone (hgh) immunosuppressants such as tacrolimus and cyclosporine A, peptide drugs such as those described herein, including octreotide, salmon calcitonin, desmopressin, somatostatin, antibodies and antibody fragments, nucleic acids including antisense and interfereing nucleic acids (e.g. siRNAs) and vaccines.

In one preferred aspect of the present invention, the composition of the invention is such that an $I_2$ or $L_2$ phase, or a mixture thereof is formed upon exposure to aqueous fluids and a polar active agent is included in the composition. Particularly suitable polar active agents include peptide and protein actives, including those listed below. Of particular interest in this aspect are the peptides octreotide and other somatostatin related peptides, the polar active chlorhexidine (e.g. chlorhexidine digluconate or chlorhexidine dihydrochloride) and bisphosphonates (e.g. ibandronate, zoledronate, alendronate, pamidronate, tiludronate etc.).

One particularly suitable class of active agents for inclusion in any appropriate aspect of the invention are the peptide/protein actives. These include; hormones & hormone derivatives such as somatotropin, somatostatin (& analogues), calcitonin (human or salmon), oxytocin, gonadorelin (and derivatives such as leuprolide; goserelin and triptorelin), vassopresin, (and derivatives such as desmopressin and felypressin), follitropin-alpha and -beta, human chorionic gonadotropin-beta, thyrotropin alpha, secretin (e.g. porcine), bradykinin, hypotensive tissue hormone, insulin α and insulin β; antiviral, antibacterial and antifungal peptides including, interferon-alpha 1/13, interferon-alpha 2, interferon-beta, interferon-gamma, (including recombinant forms), tachyplesin i, tuftsin, magainin i and ii, indolicidin (e.g. bovine), protegrin (e.g. swine), polyphemusin i & ii, polymixin b, gramicidin s; interleukins (ils) including il-1 alpha, hematopoietin-1, il-1 beta, catabolin, il-2, t-cell growth factor (tcgf) (aldesleukin), il-3, haematopoietic growth factor, il-4, b-cell stimulatory factor, il-5, t-cell replacing factor, il-6, b-cell stimulatory factor, il-7, il-8, neutrophil-activating, il-9, t-cell growth factor p40, il-10, cytokine synthesis inhibitory factor, il-11, adipogenesis inhibitory factor, il-13, il-15, il-17, cytotoxic t lymphocyte-associated antigen 8, il-18, interferon-gamma inducing factor, il-19, melanoma differentiation associated protein-like protein, il-20, four alpha helix cytokine zcyto 10, il-24, melanoma differentiation associated protein 7, il-26; and other peptides & proteins, including intercellular adhesion molecule 1, pneumadin, alteplase, interleukin-1 receptor antagonist, gmcsf, filgrastim (g-csf), lepirudin, becaplermin, ospa, avicine, tubulysins a-f, contakulin g (cgx-160), alpha conotoxin-like peptides, (see wo 02/079236), and mellitin.

In the methods of treatment of the present invention, as well as in the corresponding use in therapy and the manufacture of medicaments, an active agent is not always necessary. In particular, lipids, particularly phospholipids such as PC have been implicated as highly beneficial in themselves for the treatment of certain conditions (including those described herein below). Without being bound by theory, it is believed that suitable lipids, such as those in the formulations of the present invention, form protective layers over and around many structures of the body, such as the linings of many body cavities and the contact surfaces of joints. These layers may serve as protection from adhesion and attack by a wide variety of chemical and biological agents (such as on gastric surfaces and in the lining of the GI tract), may act as lubricants (particularly in joints but crucially also on the linings and membranes surrounding many internal structures such as heart and lungs), and may additionally contribute to cell wall repair by allowing lipid exchange and dilution of undesirable membrane-bound and membrane-soluble agents. The lipid nature of the compositions also forms a harmless substrate for unwanted inflammatory lipase enzymes such as phospholipases such as phospholipase $A_2$ ($PLA_2$).

In an alternative embodiment of the methods of treatment and corresponding uses of the present invention, suitable actives may be included, either as the sole beneficial agent, or to complement the effect of suitable lipid components. Suitable actives will typically be suitable for the treatment of inflammation and/or irritation, such as steroidal and non-steroidal anti-inflammatory drugs and local immune modulators. Examples of such agents are well known and include corticosteroids such as prednisone methylprednisolone and hydrocortisone, and derivatives of nonsteroidal anti-inflammatory compounds such as benzydamine, paracetamol, ibuprofen and salicylic acid derivatives including acetyl salicylate and 5-amino salicylates. Local inhibitors of inflammatory pathways are also suitable, including the antigen recognition suppressors methotrexate, azathioprine or 6-mercaptopurine and phospholipase inhibitors, such as $PLA_2$ inhibitors. In this context it is noteworthy that the composition of the invention is suitable for intra-articular administration into the synovial fluid where phospholipids in addition to being controlled release carriers have known beneficiary effects relating to joint lubrication.

Suitable loadings for the active agents will be established by reference to their known doses, bearing in mind the route of administration and that the compositions of the invention may provide a greater biological uptake of active agent than known formulations.

One particularly advantageous aspect of the compositions of the invention is that a very high level of active agent can be incorporated. In particular, compositions containing a proportion of water or a cosolvent (as described herein), are highly effective in solubilising high levels of active agents of many types. The compositions may thus contain at least 2% of an active agent, preferably at least 5% and more preferably at least 10% of an active agent. Advantageously, up to 20% by weight of active agent may be incorporated.

The amphiphile based particles of the invention (including those formed or formable from the compositions of the invention) may desirably also be modified with surface active agent(s) (especially a polymer) e.g. a starch or starch derivative, a copolymer containing alkylene oxide residues (such as ethylene oxide/propylene oxide block copolymers), cellulose derivatives (e.g. hydroxypropylmethylcellulose, hydroxyethylcellulose, ethylhydroxyethylcellulose, carboxymethylcellulose, etc) or graft hydrophobically modified derivatives thereof, acacia gum, hydrophobically modified polyacrylic acids or polyacrylates, etc. The surface active polymer may also be used to provide a functional effect on the surface of the particles, for example, in order to selectively bind or target the particles to their desired site of action. In particular, polymers such as polyacrylic acids, hyaluronic acids, gellan gum or chitosans may be used to provide mucus adhesive particles. Such particles will thus tend to remain localised, thus increasing the spatial control over the active agent release. Compositions of the invention comprising such surface modified particles form a further embodiment of the invention.

In colloidal compositions, the average particle size will typically be in the range 0.1 to 0.6 µm, for example as determined by light scattering methods (e.g. laser diffraction). Preferably, no more than 1% of particles will be outside the range 0.05 to 1.5 µm, more preferably, not more than 0.1% will be outside this range, and most preferably no detectable (by laser diffraction) proportion of particles will be outside this range. In non-colloidal formulations the average particle size will typically be in the range 10 to 200 µm.

A highly significant advantage of the present invention is, furthermore, that the colloidal formulations are typically physically stable to storage over extended periods at ambient temperature. Such formulations should be essentially stable in terms of phase behaviour, particle size and particle size distribution for periods of at least 10 days at room temperature, more typically at least 3 months, preferably at least 6 months and more preferably 12 months or more. In contrast, known dispersions of similar particle size may have particle sizes stable for less than 10 days at room temperature (see e.g. Kamo et al supra) This is a particular advantage of compositions of the present invention comprising components a+b+c, since compositions of components a+b in the absence of component c are typically less stable to storage.

A particle size distribution can be considered essentially stable to storage if the mean particle size increases no more than two fold during the storage period. Preferably, the mean size should increase no more than 50% and more preferably no more than 20% during the storage period. Similarly, the width of the distribution at half-height should preferably increase by no more than 50%, more preferably by no more than 20% and most preferably no more than 10% during the storage period. Where a distribution is monomodal, it should preferably remain monomodal during the storage period. In a highly preferred embodiment, the particle size distribution of the compositions of the invention alters in mean particle size and particle size distribution width at half-height by no more than 10% and remains monomodal on storage for the periods indicated above.

It is particularly important in the case of colloidal dispersions for use in intravenous or intra-arterial administration that the particle size distribution be stable during storage and use. A composition containing even a relatively small component of non-colloidal particles may cause embolism, or at least unpredictable rates of release upon administration directly to the blood stream. Similarly, the controlled release of an active agent may be dependent upon a reliable particle size distribution in a composition for administration by any other route. Pharmaceutical, diagnostic and veterinary products are also desirably stable to storage for several months or the cost and availability of the product is significantly adversely affected.

In an additional important and highly preferred embodiment of the invention, liquid compositions of the invention may be prepared as solvent mixtures. Such liquid precursors will comprise components a, b, c, a cosolvent and optionally an active agent. The liquid precursors containing an active agent can, for example, be filled in capsules and non-lamellar particles form when contacted with GI-fluid. Similarly, a liquid precursor may be provided in an ampoule for dispersion in a fluid (e.g. isotonic saline) prior to injection or may be injected directly and form non-lamellar particles in vivo upon contact with a body fluid. Most importantly the present inventors have unexpectedly discovered that by varying the amount of component c it is possible to tune the in vivo release duration in the time window from a few hours up to several weeks. Furthermore, high initial drug concentrations can be avoided thus reducing potential local and systemic side effects.

Co-solvents should generally be miscible or at least partially soluble with water and should be tolerable in the application in which the composition will be used. Organic solvents having 1 to 6 carbon atoms and preferably at least one oxygen substituent and water-soluble polymers thereof are preferred. Suitable classes of co-solvents are alcohols (including polyols), ketones, esters, ethers, and polymers thereof. Typical co-solvents are ethanol, isopropanol, N-methyl-2-pyrrolidone (NMP), propylene glycol, PEG400 and glycerol. Ethanol is particularly suitable. The solvent may be added at a level up to about 10 to 20% (by weight) of total lipid.

The compositions of the present invention may be formed by preparing a dispersion of components a, b, and c in a solvent (such as an aqueous solvent) and then optionally treating the dispersion with one or more cycles of heating and cooling.

Dispersions of particles comprising components a, b and c are formed as pre-formulations prior to the optional heat treatment cycles. This pre-formulation may be prepared by established methods, such as those indicated in the present Examples and in U.S. Pat. No. 5,531,925, WO 02/02716, WO 02/068561, WO 02/066014 and WO 02/068562 and may itself be a composition of the invention. The disclosures of these and all references cited herein are hereby incorporated herein by reference. Such methods include:

i) Adding an amphiphile/water liquid crystal phase (such as component a in water) to an aqueous solution of fragmentation agent (such as components b and/or c) and either allowing natural fragmentation of the mixture or accelerating the process with, for example, mechanical agitation, vortexing, roto-stator mixing, high-pressure homogenization, microfluidisation and/or ultrasound; or ii) Adding a mixture of a+b+c (optionally containing at least one bioactive agent) to a solvent (e.g. aqueous solution) and agitating directly.

A further method by which dispersion containing active agents may be prepared, particularly from liquid crystalline phases, is by dissolution in super-critical carbon dioxide (sc-$CO_2$) or an alternative processing solvent, such as light alcohols (e.g. methanol or ethanol), suitable for dissolving and lowering the viscosity of the composition. In particular, liquid crystalline phase, such as bulk cubic or hexagonal phase, is often highly viscous and can be difficult to handle and mix. Consequently, if the liquid crystalline phase is to be prepared as a bulk liquid and subsequently loaded with active agent, the mixing required to provide even distribution of the active agent is difficult to achieve. In the super-critical region of the pressure/temperature diagram (typically at room temperature or above and at 150 bar or greater), carbon dioxide forms a highly effective solvent and may be used to reduce the viscosity of the liquid crystalline phase and promote effective mixing and loading with active agents. The sc-$CO_2$ may then be removed (e.g. by reducing the pressure) and the loaded bulk phase dispersed in solvent, as discussed above. The use of sc-$CO_2$ in formation of active-agent loaded dispersed liquid crystalline phases (especially those of the present invention) thus forms a further aspect of the invention.

The phase behaviour and size distribution of particulate formulations of the invention may be controlled by one or more (preferably one) cycles of heating and cooling. Such cycles can be used to convert lamellar particles to non-lamellar form, and/or to reduce the spread of particle sizes. The stability of the particles may also be improved by this method.

A heat cycle brings the composition, with or without the active agent present, up to a temperature sufficient to provide conversion of at least a portion of the particles to non-lamellar phase upon cooling to ambient temperature. This will typically involve heating to around 90-150° C. for 1-30 min followed by cooling to ambient temperature. More typically a heat cycle will involve heating to 100-120° C. for 2-20 minutes before cooling. The most suitable conditions will vary in detail between compositions but will be readily established by the skilled worker.

In the heat cycling process, the mean particle size typically increases slightly but the particle size distribution is reduced.

In a further aspect, the present invention thus also provides a method for the formation of non-lamellar particles comprising forming a mixture comprising;
a) 5 to 90% of at least one phosphatidyl choline component,
b) 5 to 90% of at least one diacyl glycerol component, at least one tocopherol, or mixtures thereof, and
c) 2 to 40% of at least one non-ionic stabilising amphiphile, wherein all parts are by weight relative to the sum of the weights of a+b+c and dispersing said mixture in an aqueous fluid. The method preferably also comprises at least one heating and cooling cycle as described herein and the aqueous fluid may be water, an aqueous solution suitable for injection, a body fluid or any other suitable fluid as indicated herein. The mixture may consist purely of the amphiphiles a-c or may also contain other components such as active agents and/or water miscible solvents, as illustrated in the Examples below. The method is also optionally followed by a drying step (such as spray drying or freeze drying) whereby to form the compositions into the form of a powder.

The presence of particles in non-lamellar form will preferably be assessed from a set of cryo-transmission electron microscopy particle images, preferably showing a sample of more than 20, preferably more than 30 and most preferably at least 50 particles. The presence of non-lamellar particles may also be assessed by X-ray scattering experiments.

Since the heat treatment method can be used to convert lamellar particles to non-lamellar form, it is not essential that the pre-formulation particles be non-lamellar. Thus, any of the well-known methods for formulating lipids into vesicles may be used to create pre-formulations for use in heat treatment methods of the present invention. Suitable methods include, for example, sonication or extrusion (such as through a polycarbonate membrane). Such methods will be well known to those of skill in the appropriate art.

The pre-formulations should, preferably, be formulated such that the thermodynamically stable state at ambient temperature is non-lamellar this will generally be the case due to the specific choice of components a, b and c, and the proportions thereof. Alternatively, the non-lamellar form may be a thermodynamically meta-stable state. Where present, the active agent may be incorporated into the particles prior to and/or after heat cycling. Where more than one heat cycle is used, the active agent may be incorporated between cycles. Where the active agent is heat sensitive (e.g. peptide or protein) the active agent is preferably incorporated after heat cycling is complete. In contrast, where the active agent is stable to the heat cycling method, this method (heat cycling in the presence of the active agent) can be used to provide very high loading levels of active agent, which remain stable for long periods.

The particles (which may have been heat treated or may be subsequently heat treated) may be concentrated (e.g. by ultra-filtration or dialysis) and/or dried, for example by spray drying, fluid bed drying or freeze drying. In the case of dried particles, the drying process may be followed by particle size enlargement through single or repeated agglomeration and granulation steps. The concentrated, dried and/or agglomerated particle formulations thus formed may be used as such or hydrated and/or dispersed to yield non-lamellar particle dispersions suitable for use in the delivery of active substances, especially in vivo. Such concentrated, dried and/or agglomerated particle formulations and the dispersions resulting from their re-suspension/hydration form a further aspect of the present invention.

The dry (by which is meant functionally dry rather than being completely devoid of solvent) powder compositions of the invention may be resuspended to give colloidal or non-colloidal dispersions in a suitable (especially aqueous) fluid. Alternatively, the dry compositions may be dissolved in a suitable co-solvent, as described herein, and administered whereby to form non-lamellar structures in vivo upon contact with a body fluid. These aspects of the invention are particularly suited for intramuscular and/or subcutaneous injection and may form a long-lasting non-lamellar structure from which active agent may be slowly released over a period of days or weeks. Such slow-release formulations may be generated from any suitable composition of the invention but are particularly suited to generation from re-suspended powders.

Semi-solid (e.g. gel, waxy solid) compositions may be prepared by use of a polymeric agent in the compositions of the invention. Such semi-solid precursors will comprise compositions of the invention as described herein and additionally at least one polymeric solidifying agent. Typically, such compositions comprise components a, b, c, a polymeric agent, optionally a co-solvent and optionally an active agent. The semi-solid precursors are typically liquefiable by heat and can, for example, be filled in capsules, moulded etc. The semi-solid compositions of the invention may be resuspended to give colloidal or non-colloidal non-lamellar particle dispersions in a suitable (especially aqueous) fluid. Alternatively, non-lamellar structures form when contacted with aqueous body fluids e.g. GI-fluid. The polymeric solidifying agent is a preferably biotollerable polymer, preferably having a melting point between 35 and 100° C., more preferably 40-95° C. and most preferably 45-90° C. A particularly preferred polymeric agent is polyethylene glycol (PEG) with molar mass in the range of 950-35000, most preferably 1000 to 10,000. PEG 4000 is a highly preferred example.

The formulations of the present invention comprise at least one composition of the invention and at least one suitable carrier or excipient. Where the formulation is a pharmaceutical formulation, the carriers or excipients will be pharmaceutically tolerable.

The compositions may be formulated with conventional pharmaceutical carriers, diluents and/or excipients such as aqueous carriers (e.g. water for injections), binders, fillers, stabilizers, osmolality adjusting agents, antioxidants, effervescing agents, pH buffers and modifiers, viscosity modifiers, sweeteners, lubricants, emulsifiers, flavours, coating agents (e.g. gastric juice resistant coatings) etc.

Formulations comprising a composition of the invention and at least one pharmaceutically acceptable carrier and/or diluent may be formulated in any known dosage form including as suspensions in liquid, powders, tablets, capsules, coated capsules, coated tablets, aerosols, suppositories, drops, creams, transdermal patches, sprays etc. Where the composition of the invention has been dried, this may be formulated in a suitable form (such as a powder) for resuspension in an appropriate medium (such as purified water or a solution of physiological osmolality) prior to administration. The formulations and pharmaceutical compositions may be administered by any suitable method including orally, ophthalmicly, by inhalation, parenterally (e.g. by intramuscular, subcutaneous or intravenous injection or infusion), topically, rectally etc. Parenteral compositions are preferred since the present invention provides a remarkable combination of high stability (in particle size and phase structure) and very low parenteral toxicity. Topical compositions are, however, also highly effective and pump-spray or pressurised spray dispersions may be used for dermal, nasal, and intraoral (especially buccal) applications. Rectal administration as a concentrated dispersion or solidified suppository are also highly suitable.

The formulations, compositions and methods of the invention relating to the treatment of inflammation or irritation, are particularly suitable for addressing inflammation and/or irritation in a body cavity. Administration to a body cavity is thus highly suitable in this aspect and will be carried out by a method suitable for the cavity being treated. Mouthwashes, for example, may be suitable for oral or buccal cavities, while other parts of the GI tract may be suitably treated by oral formulations, including dispersions and dry pre-formulations, and rectal formulations such as enemas or suppositories. Rinses and pesseries are similarly suitable for vaginal delivery.

The compositions of the present invention are highly suitable for treating inflammation in a body cavity because of the highly bioadhesive mature of the non-lamellar phase and the resulting long-lasing effects. The ability of the formulations to comprise or disperse into non-lamellar particles, which are then easily transported and distributed around the site of application is also of importance, as well as the inherently soothing and highly biocompatible nature of the constituents.

The methods of treatment and corresponding uses of the present invention are thus most applicable to inflammatory diseases and inflammation caused by, for example, wounding or abrasion. Especially suitable are inflammatory diseases affecting at least one body cavity. Diseases of the GI tract are highly suitable for treatment with the compositions of the present invention, particularly inflammatory bowel disease including Crohn's disease and ulcerative collitus. Similarly, application to a body cavity during surgery may also be used to take advantage of the properties of the formulations. They may thus be directly applied, for example by spraying or painting, to sooth inflammation resulting from or exposed during surgery and also to reduce the tendency of surgically manipulated tissue to "stick" and/or form adhesions/bridges at unwanted sites.

A particular advantage of the compositions of the present invention is their remarkably low toxicity, particularly when administered parenterally. In particular, the present compositions can show a remarkably low acute toxicity when administered by intravenous injection. In a preferred aspect, the present invention thus provides compositions of the invention showing no acute toxicity by intravenous injection in rats to a level of at least 200 mg/kg body weight, preferably at least 600 mg/kg and more preferably at least 1 g/kg body weight.

As mentioned a further key advantage of the compositions of the present invention is that they can be used to generate "short term" depot compositions. In particularly, immediate release formulations of active agents are common and coatings etc can sometimes be used to provide formulations that will release active agents over a period up to around 12 hours. In contrast, long-acting "depot" injections typically comprise solutions or suspensions of polymers, such as poly-lactate-co-glycolate, or implanted physical pumps, which are driven by osmotic pressure. These methods typically provide release over a period of a month or more and typically require complex preparation and/or administration. In contrast, there are few methods for releasing active agents over a 1-30 day period, especially over a 1-14 day period, and most preferably over a 2-7 day period, as might be required, for example, for post-operative analgesia or a course of antibiotics. The compositions of the invention have one of more of the following advantageous properties provided as a result of their specific composition:

They provide ready-to-inject compositions with little or no preparation required;

They avoid the lengthy preparation and administration typically required for depot products;

They can be injected directly from a pre-filled injection device containing the composition (which also forms an aspect of the invention);

They are stable to storage, as indicated above;

They can be injected through a fine bore needle (e.g. less than 20 gauge, preferably 23 gauge or less, more preferably 27 gauge or smaller);

They can be injected effectively intramuscularly or subcutaneously or intracavitary;

High levels of active agent can be incorporated (as indicated herein);

A specifically favoured short-duration depot is one comprising a composition of the present invention with GLP-1 or an analogue or derivative thereof (preferably at a dose of 0.1 to 20 mg) for subcutaneous or intramuscular injection. Such a depot could provide sustained release of the GLP-1 analogue over 2-14 days, preferably 5 to 10 days. The most suitable use for such a composition would be in the treatment of diabetes (especially type II) or in the manufacture of a medicament for such a use.

Glucagon-like peptide (GLP)-1 is a potent glucoregulatory hormone that is released from intestinal L cells into the circulation in response to nutrient ingestion and neural and endocrine stimuli. Structurally, GLP-1 is a 37-amino acid peptide with a MW of 4.2 KDa, having a sequence highly conserved between different species. GLP-1 is involved in modification of glucose homeostasis through actions that include potentiation of glucose-stimulated insulin secretion and biosynthesis and suppression of glucagon secretion, gastric emptying, and food intake. The abilities of GLP-1 to stimulate insulin secretion and inhibit glucagon release are glucose-dependent; thus, the risk of hypoglycemia with GLP-1 administration is low. GLP-1 also increases beta-cell mass in preclinical models of diabetes through mechanisms that include stimulation of beta-cell proliferation and neogenesis and inhibition of beta-cell apoptosis. Studies in both animals and humans indicate that GLP-1 may also play a protective role in the cardiovascular system.

The combined actions of GLP-1 have generated substantial interest in using this peptide as a therapeutic agent for the treatment of type 2 diabetes. However, the therapeutic potential of native GLP-1 is limited by its very short plasma half-life (below 2 minutes). This is due to both rapid inactivation by the proteolytic enzyme dipeptidyl peptidase (DPP)-IV and renal clearance. Consequently, long-acting, DPP-IV-resistant GLP-1 analogs have been developed for clinical use, including exenatide (Byetta, Amylin-Lilly), liraglutide (Novo Nordisk), CJC-1131 (ConjuChem), AVEO10 (Zealand Pharma-Sanofi-Aventis), LY548806 (Lilly), and TH-0318 (TheraTechnologies). All these are once- or twice-daily administration products; a controlled-release (one week) exentide product (Alkermes-Amylin-Lilly) is currently under clinical investigation. These GLP-1 mimetics bind to GLP-1 receptors with similar affinity and produce biological actions identical to those of native GLP-1 but are resistant to DPP- IV-mediated inactivation and renal clearance. These compounds are able to exert more sustained GLP-1-like activity for longer periods of time in vivo. An alternative therapeutic approach for prolonging the action of native GLP-1 is to inhibit DPP-IV activity, thereby preventing GLP-1 degradation. Several orally active agents that inhibit DPP-IV activity are being evaluated for the treatment of type 2 diabetes.

In a still further aspect, the present invention provides a kit for the preparation of a composition of the present invention in the form of a suspension, said kit comprising at least one composition of the present invention in the form of a powder and optionally and preferably instructions for suspending the powder in an aqueous fluid.

The invention will now be further illustrated by reference to the following non-limiting Examples and the attached figures, in which.

ABBREVIATIONS

SPC=Soy bean phosphatidylcholine from Lipoid GmbH, Germany
GDO=Glyceroldioleate from Danisco, Denmark
P80=Polysorbate 80 from Apoteket, Sweden
Solutol® HS 15=Macrogol 15 Hydroxystearate from BASF, Germany
Cryo-TEM=Cryogenic-Transmission Electron Microscopy
PPF=Propofol from Sigma-Aldrich, Sweden
EPC=Egg Phosphatidylcholine from Lipoid GmbH, Germany
DOPE-PEG(5000)=Dioleoyl phosphatidyl ethanolamine poly(ethylene glycol) 5000 from Avanti Polar Lipids, U.S.A.
CMC=Carboxy Methyl Cellulose (sodium salt) from Sigma-Aldrich, Sweden
PVP=Polyvinyl pyrrolidone from ISP, U.S.A.
PEG=Polyethylene glycol from Merck, U.S.A.

EXAMPLE 1

Non-Lamellar Reversed Phase Nanoparticles 1.1—Preparation of a Non-Lamellar Dispersion A dispersion of non-lamellar (>80% by weight of amphiphile) and lamellar (<20% by weight of amphiphile) particles, was formed by mixing 2.125 g of a SPC/GDO 40/60 wt/wt mixture (formed by mixing the lipids in ethanol and thereafter evaporating the solvent) and 0.3826 g of P80. The components were molecularly mixed by heating for 5 min at 70° C. and vortexing. The homogenous lipid melt (2.012 g) was added drop wise to 38.01 g of deionized water. The resulting coarse dispersion was put on a shaking table (350 rpm) and shaken for 24 hours to give a turbid homogenous dispersion.

The particle size was measured using laser diffraction (Coulter LS230). The size distribution was found to be narrow and monomodal with a mean particle size of 95 nm.

1.2—Heat Treatment

An optional cycle of heat treatment was carried out on the dispersion prepared in Example 1.1.

Figure 1:
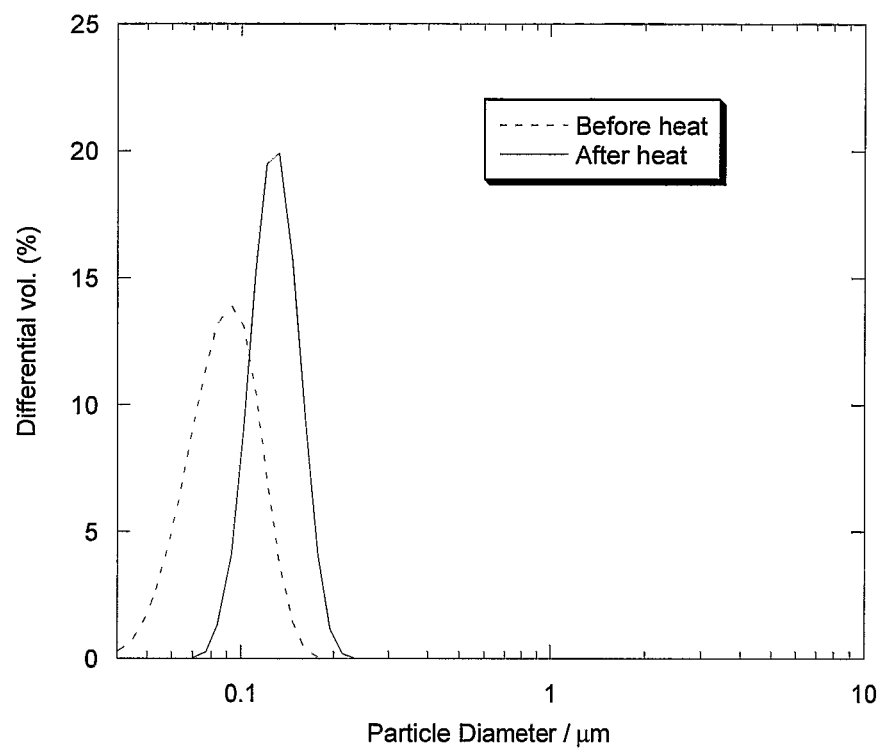
FIG. 1 shows the particle size distributions of a dispersed non-lamellar SPC/GDO/P80 sample before and after heat treatment.

A sample of the dispersion generated in Example 1.1 (25 mL) was autoclaved (125° C., 20 min) and cooled to room temperature. The particle size distribution was narrowed, the mean particle size increased to 137 nm and when examined by Cryo-TEM, a still greater proportion of the particles showed non-lamellar character. The particle size distribution before and after heat treatment is shown in FIG. 1.

Components:

| Formulation | a:b:c | abc wt % | medium | aq wt % | Phase before | Temp ° C. | Time min | Phase after |
|---|---|---|---|---|---|---|---|---|
| i | 33.9:50.8:15.3 | 5.0 | deionized water | 95 | Non-lamellar | 125 | 20 | Non-lamellar | a SPC
b GDO
c P80

EXAMPLE 2

Further Composition

The effect of adding a higher concentration of stabilizing agent was considered by preparing a second composition by the method of Examples 1.1 and 1.2. A solution of SPC and GDO (40/60 wt/wt) (2.017 g) and P80 (0.514 g) were molecularly mixed by heating for 5 min at 70° C. and vortexing. The homogenous lipid melt (2.006 g) was added drop wise to 38.00 g of deionized water. The resulting coarse dispersion was put on a shaking table and shaken for 24 hours to give a turbid homogenous dispersion. The dispersion was thereafter heat-treated according to Example 1.2.

Figure 2:
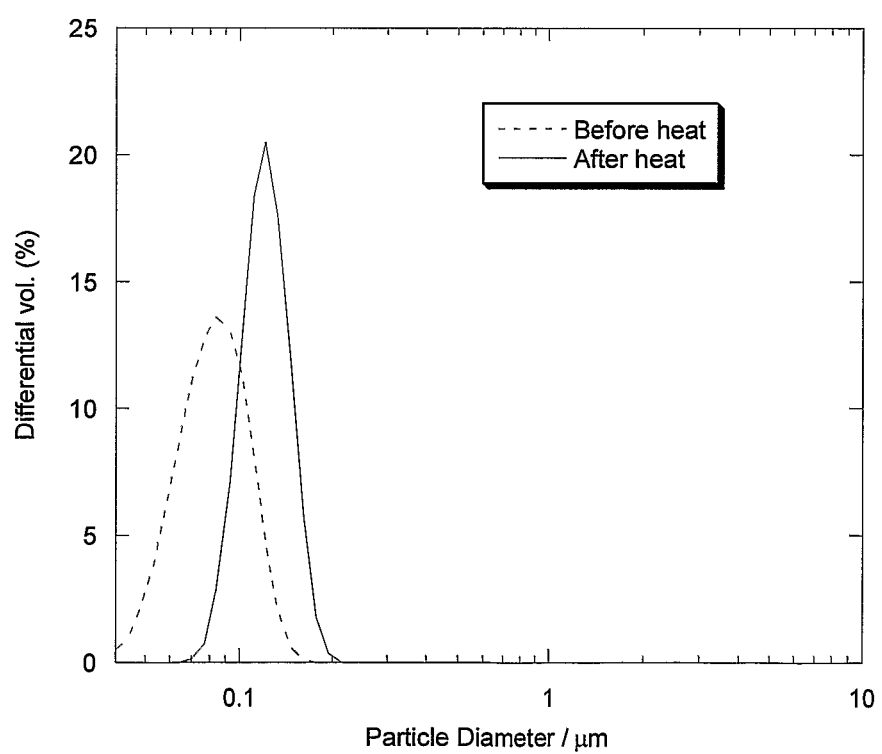
FIG. 2 shows the particle size distributions of a dispersed non-lamellar SPC/GDO/P80 sample before and after heat treatment.
Figure 3:
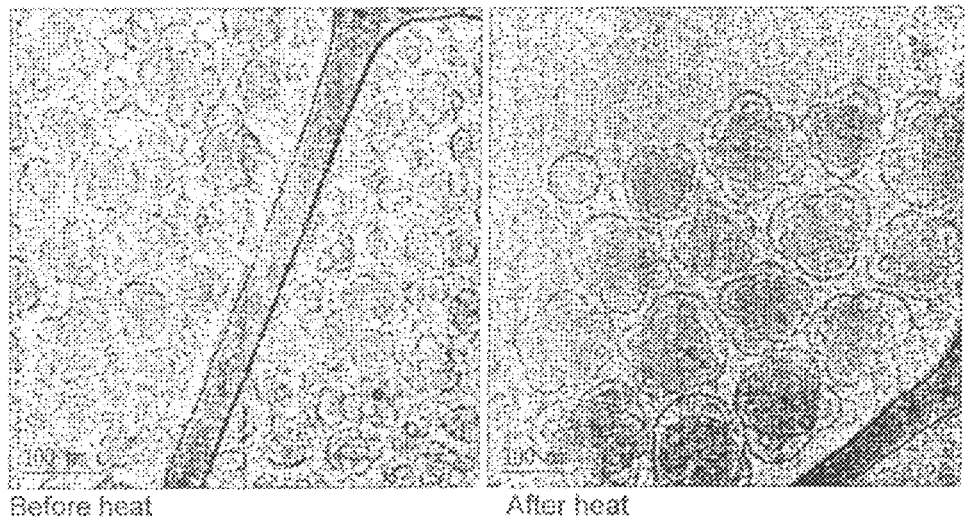
FIG. 3 shows cryo-transmission electron micrographs of a dispersed non-lamellar sample of SPC/GDO/P80 before and after heat treatment.

The size distributions before and after heat treatment were found to be narrow and monomodal with the mean particle size being 88 and 129 nm, respectively. The heat treatment also narrowed the size distribution as indicated in FIG. 2. Cryo-TEM images were obtained from the samples before and after heat treatment as shown in FIG. 3. The cryo-TEM results clearly evidence the formation of non-lamellar nanoparticles of uniform size containing a disordered inner structure of multiply connected bilayers. The particles observed after heat treatment exhibit a denser core compared to those before heat treatment.

Components:

| Formulation | a:b:c | abc wt % | medium | aq wt % | Phase before | Temp ° C. | Time min | Phase after |
|---|---|---|---|---|---|---|---|---|
| ii | 31.9:47.8:20.3 | 5.0 | deionized water | 95 | Non-lamellar | 125 | 20 | Non-lamellar | a SPC
b GDO
c P80

This particular composition is also well suited for preparing a liquid precursor of the non-lamellar phase dispersion. The same components were used in the same ratios. The components were molecularly mixed by heating to 70° C. for 5 min and vortexing. The liquid precursor formulation was also fortified with 10% by weight of a co-solvent (e.g. ethanol, N-methyl-2-pyrrolidone (NMP), propylene glycol, PEG400, glycerol) and thereafter dispersed into water (5 wt % amphiphile) with gentle shaking resulting in a milky white dispersion of non-lamellar phase particles.

EXAMPLE 3

Further Composition

The effect of adding another type of stabilizing agent was considered by preparing another composition by the method of Examples 1.1 and 1.2. A solution of SPC and GDO (40/60 wt/wt) (2.004 g) and Solutol® HS 15 (0.516 g) were molecularly mixed by heating for 5 min at 70° C. and vortexing. The homogenous lipid melt (2.042 g) was added drop wise to 38.00 g of deionized water. The resulting coarse dispersion was put on a shaking table and shaken for 24 hours to give a turbid dispersion containing some poorly dispersed macroscopic particles. To obtain a homogenous dispersion, the sample was homogenised using a Microfluidizer working at 5000 PSI and room temperature. The sample was passed through the homogeniser 5 times to obtain a milky homogenous dispersion. The dispersion was thereafter heat-treated according to Example 1.2.

Figure 4:
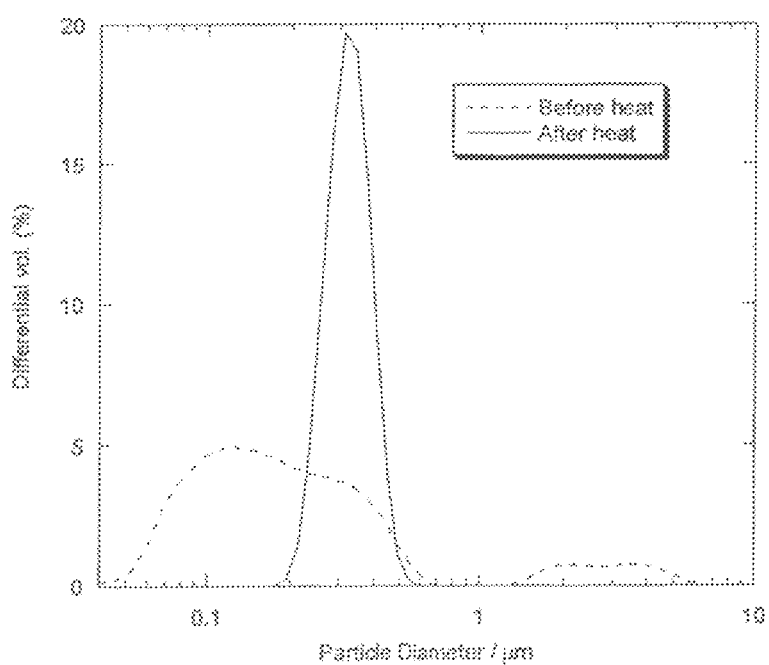
FIG. 4 shows the particle size distributions of a dispersed non-lamellar SPC/GDO/Solutol® HS 15 sample before and after heat treatment.
Figure 5:
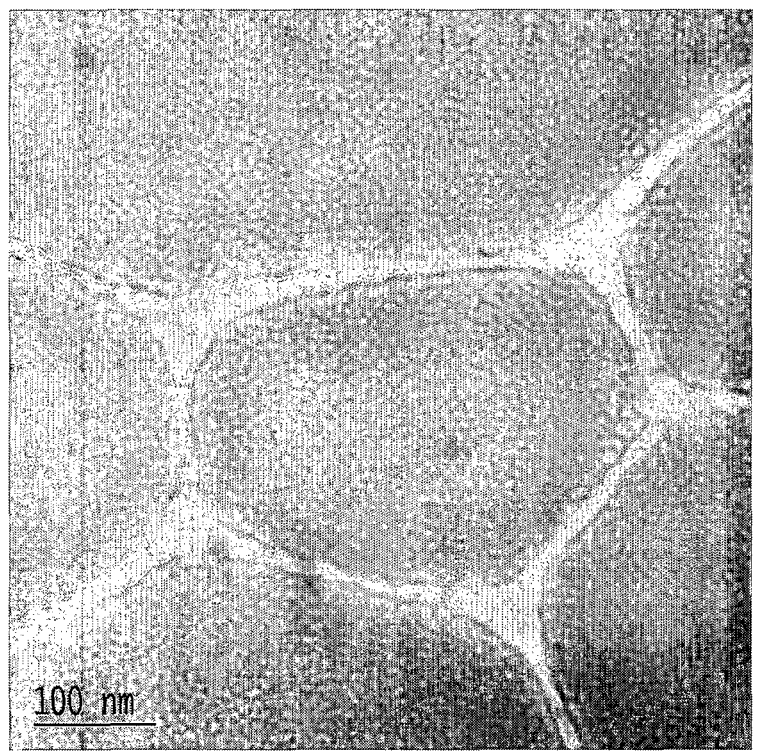
FIG. 5 shows a cryo-transmission electron micrograph of a dispersed sample of SPC/GDO/Solutol® HS 15 after heat treatment

The size distributions obtained before and after heat treatment are shown in FIG. 4 and indicate that the heat treatment step results in a monomodal and narrow distribution with the mean particle size being 343 nm. Cryo-TEM experiments after heat treatment displayed particles with dense inner non-lamellar structure as shown in FIG. 5.

Components:

| Formulation | a:b:c | abc wt % | medium | aq wt % | Phase before | Temp ° C. | Time min | Phase after |
|---|---|---|---|---|---|---|---|---|
| iii | 31.8:47.7:20.5 | 5 | deionized water | 95 | Non-lamellar | 125 | 20 | Non-lamellar | a SPC
b GDO
c Solutol ® HS 15

EXAMPLE 4

Further Composition: Concentrated Non-Lamellar Particle Dispersion

A concentrated non-lamellar particle dispersion was by prepared by the method of Examples 1.1 and 1.2. A solution of SPC and GDO (40/60 wt/wt) (4.7958 g) and P80 (0.8152 g) were molecularly mixed by heating for 5 min at 70° C. and vortexing. The homogenous lipid melt (5.001 g) was added drop wise to 44.999 g of deionized water. The resulting coarse dispersion was put on a shaking table and shaken for 48 hours (350 rpm) to give a turbid homogenous dispersion. The dispersion was thereafter heat-treated according to Example 1.2.

Figure 6:
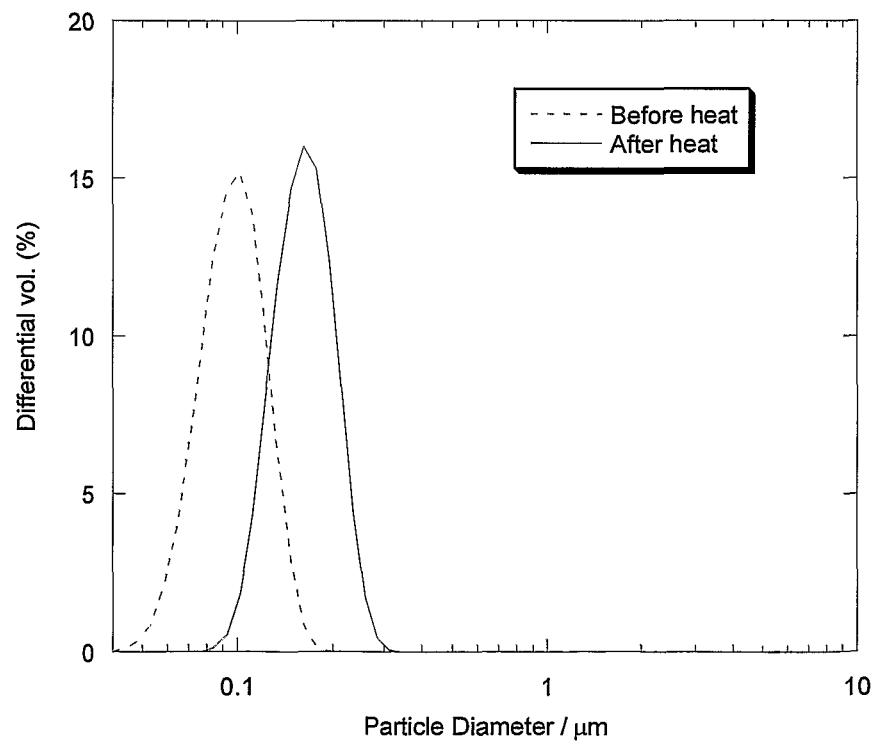
FIG. 6 shows the particle size distributions of a concentrated dispersed non-lamellar SPC/GDO/P80 sample before and after heat treatment.

The size distributions before and after heat treatment were found to be narrow and monomodal with the mean particle size being 103 and 174 nm, respectively, as indicated in FIG. 6.

Components:

| Formulation | a::b:c | abc wt % | medium | Aq wt % | Phase before | Temp ° C. | Time min | Phase after |
|---|---|---|---|---|---|---|---|---|
| iv | 34.2:51.3:14.5 | 10 | deionized water | 90 | Non-lamellar | 125 | 20 | Non-lamellar | a SPC
b GDO
c P80

EXAMPLE 5

Storage Stability

Non-lamellar dispersions were prepared according to the methods of Example 1.1 and 1.2. The compositions of the dispersions are displayed in the table below. The dispersions were stored at 25° C. and the particle size distribution was measured at regular intervals. The size distributions were found to be consistent with the original size distribution for at least 2 months storage indicating excellent colloidal and storage stability.

Figure 7:
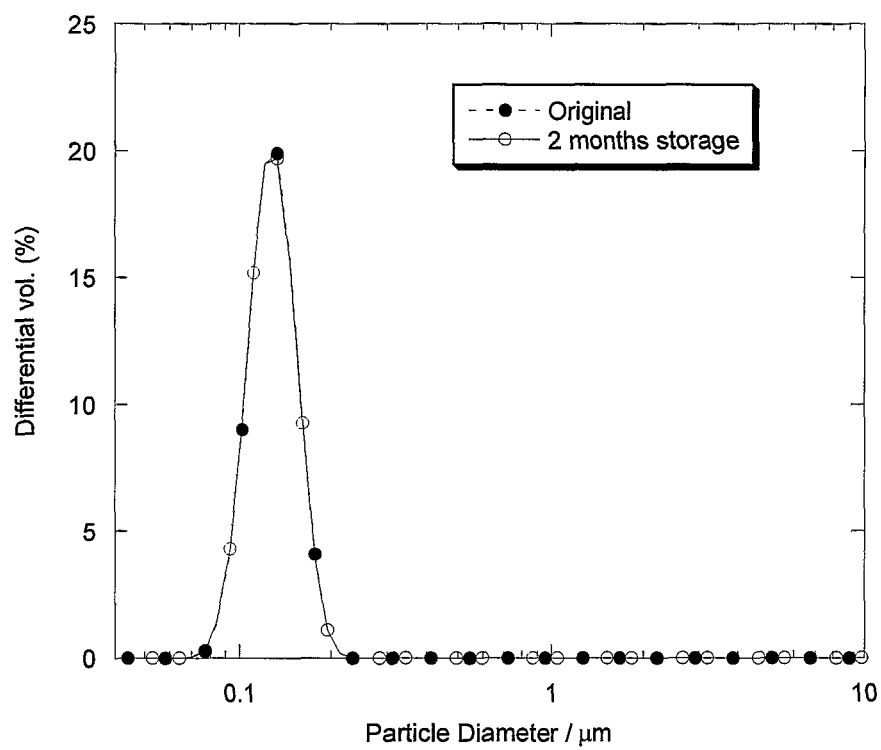
FIG. 7 shows the particle size distributions of a dispersed non-lamellar SPC/GDO/P80 sample after preparation and after storage for 2 months at 25° C.
Figure 8:
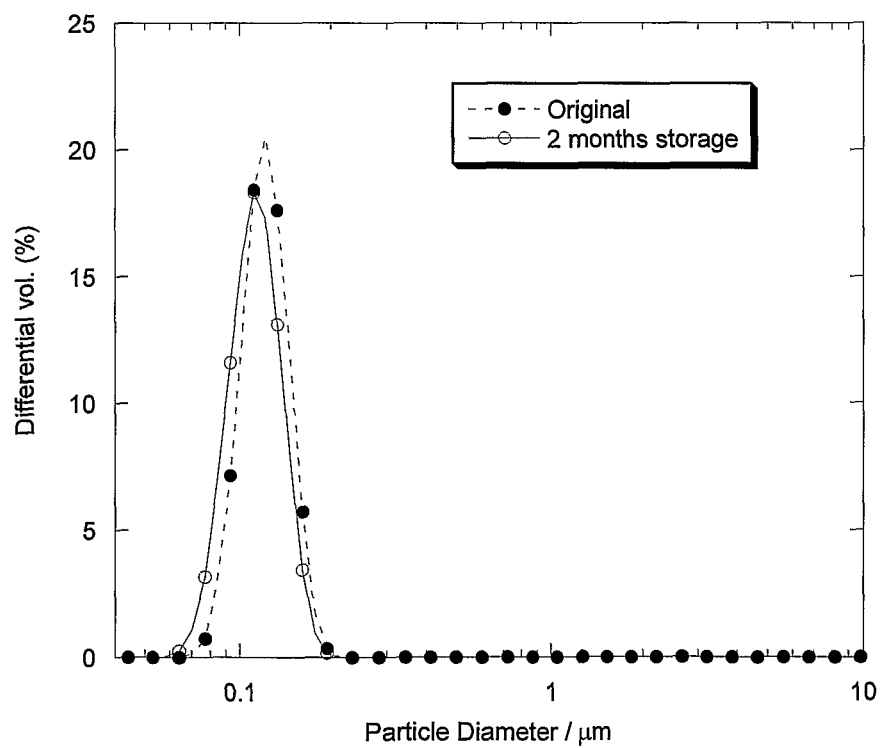
FIG. 8 shows the particle size distributions of a dispersed non-lamellar SPC/GDO/P80 sample after preparation and after storage for 2 months at 25° C.

No changes of the morphology of the non-lamellar particles could be observed (by cryo-TEM) during storage. The particle size distributions of the original dispersions and after storage for 2 months are shown in FIG. 7 (SPC/GDO/P80=34/51/15 wt %) and 8 (SPC/GDO/P80=32/48/20 wt %). As can be observed, the size distributions of the original and stored dispersions are essentially identical.

Table with compositions investigated for storage stability:

| Composition | Weight ratio | Lipid concentration (wt %) | Medium |
|---|---|---|---|
| SPC/GDO/P80 | 34:51:15 | 5 | deionized water |
| SPC/GDO/P80 | 32:48:20 | 5 | deionized water |

EXAMPLE 6

Active Agent Loading

Figure 9:
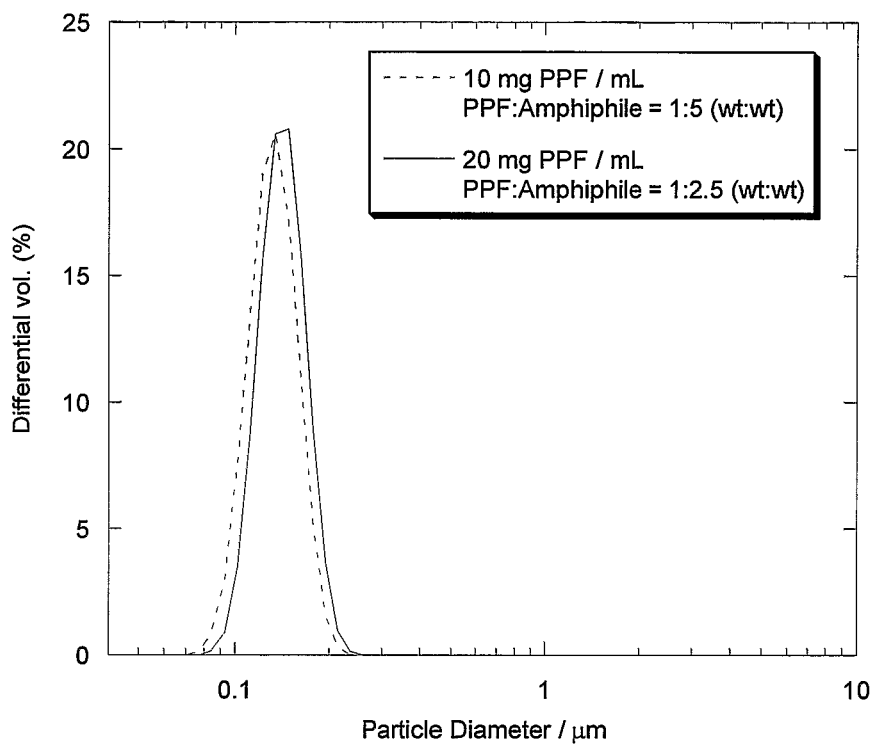
FIG. 9 shows the particle size distributions of dispersed non-lamellar SPC/GDO/P80 particle dispersions loaded with the anaesthetic agent Propofol at two different Propofol-to-amphiphile ratios.

Non-lamellar particle dispersions containing the anaesthetic active agent PPF were formed by mixing a composition comprising SPC (32% by weight of amphiphile), GDO (48% by weight of amphiphile) and P80 (20% by weight of amphiphile) with PPF at the proportions indicated in the table below. The components were molecularly mixed by heating for 5 min at 70° C. and vortexing. The homogenous lipid/PPF melt was added drop wise to an aqueous solution containing 2.5% (by weight of total formulation) of glycerol. The resulting coarse dispersions were put on a shaking table (350 rpm) and shaken for 12 hours to give homogenous dispersions. The dispersions were thereafter heat-treated by the method of Example 1.2. The particle size distributions of the resulting dispersions were narrow and monomodal with mean particle sizes in the range of 140-150 nm as shown in FIG. 9. The PPF loaded dispersions were found to be stable to storage at room temperature for at least 2 months.

Table with compositions of the final non-lamellar particle/PPF dispersions:

| Amphiphile conc. (mg/mL) | PPF conc. (mg/mL) | PPF:Amphiphile (wt:wt) |
|---|---|---|
| 50 | 10 | 1:5 |
| 50 | 20 | 1:2.5 |

EXAMPLE 7

Pharmacokinetics and Pharmacodynamics of Propofol Loaded into Non-Lamellar Particles A dispersion of non-lamellar particles containing PPF was prepared with the same composition and by the same method as in Example 6 except that the PPF concentration in this case was 10 mg/mL and the amphiphile concentration was 25 mg/mL (PPF:Amphiphile=1:2.5 wt/wt). The non-lamellar particle PPF dispersion was compared for duration of anaesthesia in rats (male SPF Sprague-Dawley rats (Mol: SPRD HAN, M&B Taconic, Lille Skensved, Denmark)) with the reference commercial Propofol Fresenius Kabi emulsion formulation (10 mg PPF/mL). The animals were given a single bolus intravenous injection of 10 mg PPF per kg body weight (induction of anaesthesia occurred directly after injection in both cases). For pharmacodynamic parameters, the time to recover (righting response time indicated by attempts to stand up) was recorded. The results are summarized in the table below indicating the high efficiency of the non-lamellar particle PPF dispersion to maintain the required anaesthetic effect.

Table with pharmacodynamic parameters:

| Formulation | Number of rats | Average Recovering Time (sec) (Std. Dev.) |
|---|---|---|
| Propofol Fresenius Kabi | 5 | 377 (89) |
| Non-lamellar Particle PPF Dispersion | 5 | 448 (60) |

Figure 10:
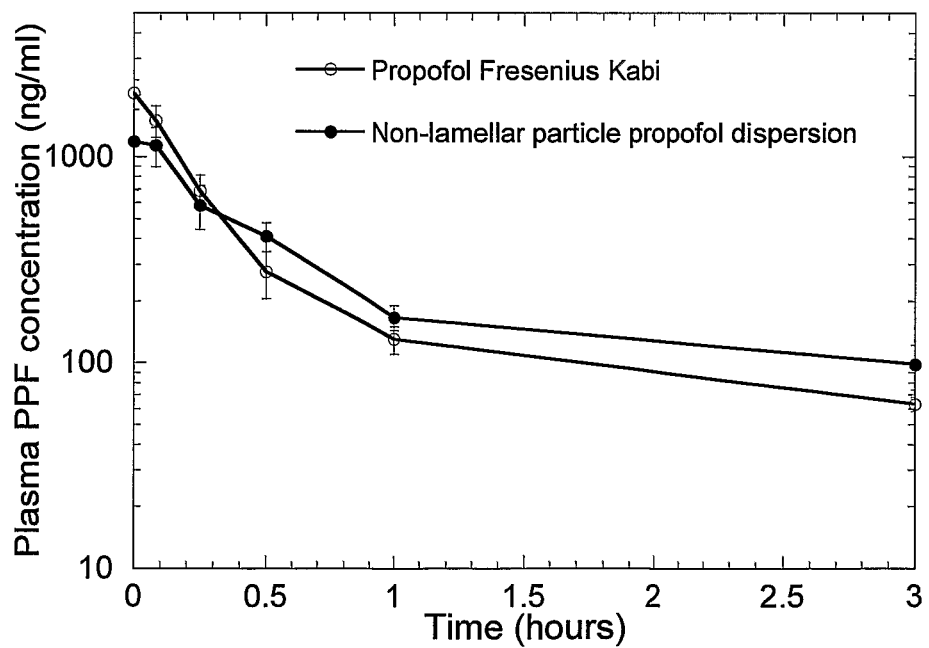
FIG. 10 shows the plasma concentration of Propofol in rat after intravenous administration.

Blood samples (0.3 mL) were collected pre-dose (one day before dosing), 5 minutes, 15 minutes, 30 minutes, 1 hr, 3 hrs, 6 hrs and 24 hrs after dosing. The Propofol concentration in rat plasma was determined by a high pressure liquid chromatography (HPLC) method known to scientists skilled in the art. Plasma concentration over time of propofol was similar for the reference formulation and the non-lamellar particle propofol formulation, respectively (FIG. 10). Terminal half-life ($t_{half}$), mean residence time (MRT), total clearance (CL), extrapolated plasma concentration at time 0 ($C_0$), and the total area-under-the-curve ($AUC_\infty$) was calculated by non-compartmental pharmacokinetic (PK) methods. $AUC_\infty$ was computed by the trapezoidal rule with extrapolation from $C_{last}$ to infinity.

Table with pharmacokinetic parameters:

| Formulation | n | $t_{half(h)}$ | MRT (h) | CL (mL/h) | $C_0$ | $AUC_\infty$ |
|---|---|---|---|---|---|---|
| Propofol Fresenius Kabi | 4 | 0.90 (0.50) | 0.88 (0.38) | 4326 (1507) | 2036 (329) | 777 (207) |
| Non-lamellar Particle PPF Dispersion | 5 | 1.97 (0.85) | 2.56 (1.25) | 2799 (568) | 1187 (501) | 1159 (243) |
| P < 0.05 (t-test) | | No | Yes | No | Yes | Yes |

It was hypothesized that administration of propofol in the non-lamellar propofol formulation would result in an increased circulation time in plasma. The observed PK parameters suggested that an increased presence of propofol was indeed achieved. This was most apparent when analyzing MRT (i.e., the time any single molecule of a drug compound is residing in the circulation), which was increased approx. 3-fold compared to the reference product. Other parameters reflecting the in vivo fate of propofol, i.e. increased $t_{half}$ and reduced CL for the non-lamellar particle propofol formulation also indicated that propofol remained for a longer time in the plasma (the differences could not be statistically verified, but the tendency was clear). Also, $AUC_\infty$ increased for the non-lamellar particle propofol formulation, implicating that the exposure to propofol was larger for this formulation than for the reference formulation at an equal dose. All observations support that the non-lamellar particle propofol formulation is capable of improving the circulation time for the active component.

EXAMPLE 8

Acute Toxicity Testing

A non-lamellar dispersion was prepared by the methods of Examples 1.1 and 1.2 using the following components:
a) SPC
b) GDO
c) P80
in the weight ratio a:b:c=34:51:15, dispersed in water to a total amphiphile concentration of 10 wt %. Sodium chloride (NaCl) was added to the dispersion to achieve 9 mg NaCl/mL.

The dispersion was thereafter tested for acute toxicity after intravenous injection in a rat model.

The non-lamellar dispersion showed no acute toxicity in a dose dependent study with doses up to 10 mL/kg of the 10 wt % amphiphile dispersion (1 g amphiphile/kg).

EXAMPLE 9

Encapsulation of a Hydrophilic, Water-Soluble Colorant

Non-lamellar particles encapsulating the highly water-soluble colorant Patent blue were prepared as follows: 3.0 g of a formulation of SPC/GDO/P80 (34/51/15 wt %) was prepared according to Example 1. To this solution, 0.15 g ethanol was added and the formulation was mixed by vortex mixing. 0.20 g of an aqueous solution of Patent blue (20 mg/mL) was added to 3.0 g of the SPC/GDO/P80/EtOH formulation. The resulting sample was mixed by vortex mixing to yield a homogenous low viscosity formulation. 2.55 g of this formulation was added to 22.5 g of deionized water and the resulting formulation was shaken at 350 rpm for 18 hours to give a homogenous blue-colored dispersion. After ultrafiltration (30000 MWCO filters) of the dispersion, the encapsulation efficiency was measured as the absorbance (at 640 nm) of the original dispersion minus the absorbance of the filtrate (unencapsulated fraction) and the difference was divided by the absorbance of the original dispersion (before all absorbance measurements, TritonX100 (10 wt % in deionized water) was added to give clear solutions).

The encapsulation efficiency was found to be 85% indicating a high potential of the non-lamellar particles to encapsulate water-soluble actives.

EXAMPLE 10

Encapsulation of a Hydrophilic, Water-Soluble Peptide

Non-lamellar particles encapsulating the water-soluble peptide octreotide were prepared as follows: 1.0 g of a formulation of SPC/GDO/P80 (34/51/15 wt %) was prepared according to Example 1. To this solution, 0.10 g ethanol was added and the formulation was mixed by vortex mixing. 0.054 g of an aqueous solution of octreotide (35.5 mg/mL) was thereafter added and the resulting sample was mixed by vortex mixing to yield a homogenous low viscosity formulation. 1.0 g of this formulation was added to 9.0 g of saline (9 mg NaCl/mL) and the resulting formulation was shaken at 350 rpm for 18 hours to give a homogenous dispersion (mean particle size of ca 100 nm). The encapsulated octreotide was separated from non-encapsulated peptide by passing 2.5 mL of the dispersion through a Sephadex G25 (PD-10) column and collecting the lipid fraction and the free octreotide fractions in separate vials. The concentration of octreotide in the lipid fraction and the free octreotide fraction was analyzed, after addition of TritonX100, by HPLC.

The encapsulation efficiency was found to be 71% again indicating the high potential of the non-lamellar particles to efficiently encapsulate water-soluble actives.

EXAMPLE 11

Non-Lamellar Particles from SPC/Tocopherol Mixtures

A solution of SPC, α-tocopherol and ethanol (27/63/10 wt %) (1.34 g) was mixed with d-α tocopheryl polyethylene glycol 1000 succinate (Vitamin E TPGS) (0.30 g). The sample was molecularly mixed by heating for 15 min at 40° C. and vortexing. The homogenous lipid melt (1.0 g) was added drop wise to 19 g of deionized water. The resulting coarse dispersion was put on a shaking table and shaken for 20 hours (350 rpm) to give a turbid homogenous non-lamellar particle dispersion.

Figure 11:
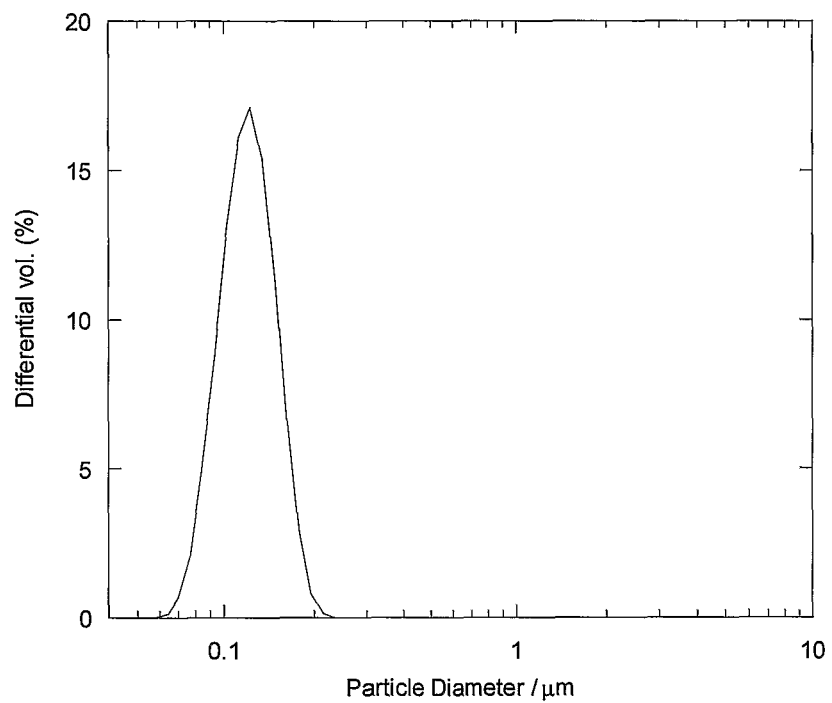
FIG. 11 shows the particle size distribution of a dispersed non-lamellar SPC/α-tocopherol/Vitamin E TPGS sample.

The size distribution was found to be narrow and monomodal with the mean particle size being 128 nm, as indicated in FIG. 11.

The dispersion was thereafter heat-treated according to Example 1.2 and cryo-TEM images of the heat-treated sample displayed non-lamellar particles containing a disordered surface structure and a dense inner non-lamellar structure.

EXAMPLE 12

The Use of EPC as a Substitute for SPC

Figure 12:
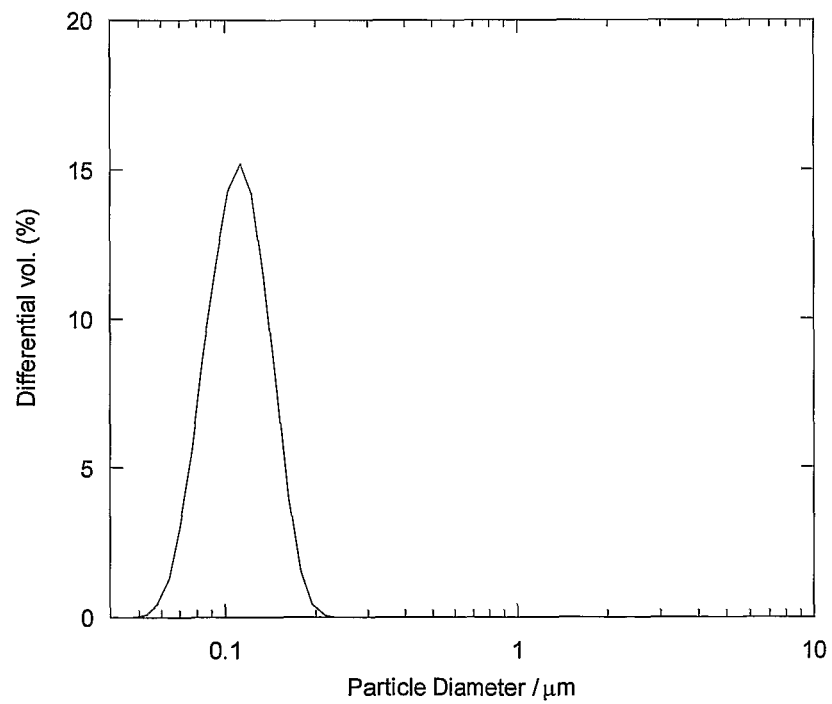
FIG. 12 shows the particle size distribution of a dispersed non-lamellar EPC/GDO/P80 sample.

EPC (1.539 g), GDO (2.302 g), P80 (0.685 g) was mixed with ethanol (0.501 g). The sample was mixed by vortex mixing and end-over-end rotation for 3 h resulting in a homogenous and clear liquid. The liquid formulation (1.665 g) was added to sterile water (28.335 g) and the resulting course dispersion was mixed for 18 h on a shaking table at 400 rpm. The dispersion obtained was homogenous and the size distribution was found to be narrow and monomodal with a mean particle size of 114 nm, as indicated in FIG. 12.

Cryo-TEM results indicated the formation of non-lamellar nanoparticles of uniform size containing a disordered surface structure of multiply connected bilayers and a dense inner non-lamellar structure.

EXAMPLE 13

Robustness of Composition

To investigate the effect of changes of the lipid composition on the facile manufacturing of non-lamellar nanoparticles, samples with a varying ratio of SPC/GDO and a constant ratio of P80 were prepared. The components were mixed with ethanol and thereafter dispersed into sterile water as described in Example 13 except for sample #1128 that was shaken for 48 h. The final compositions of the samples, the mean particle size and polydispersity index (PI) after shaking (400 rpm) and the mean particle size and polydispersity index after heat-treatment (according to Example 1.2) are indicated in the table below.

Table with compositions and data for the samples prepared in Example 14

| Sample ID | Composition (wt %) SPC/GDO/P80/EtOH/Water | Mean size/ nm (Shaking) | $PI^a$ (Shaking) | Mean size/ nm ($HT^b$) | $PI^a$ ($HT^b$) |
|---|---|---|---|---|---|
| #1128 | 2.125/2.125/0.75/0.56/94.44 | 110 | 0.24 | 141 | 0.17 |
| #1129 | 1.91/2.34/0.75/0.56/94.44 | 114 | 0.24 | 136 | 0.18 |
| #1130 | 1.70/2.55/0.75/0.56/94.44 | 116 | 0.23 | 134 | 0.19 |
| #1131 | 1.49/2.76/0.75/0.56/94.44 | 115 | 0.23 | 127 | 0.18 |

Figure 13:
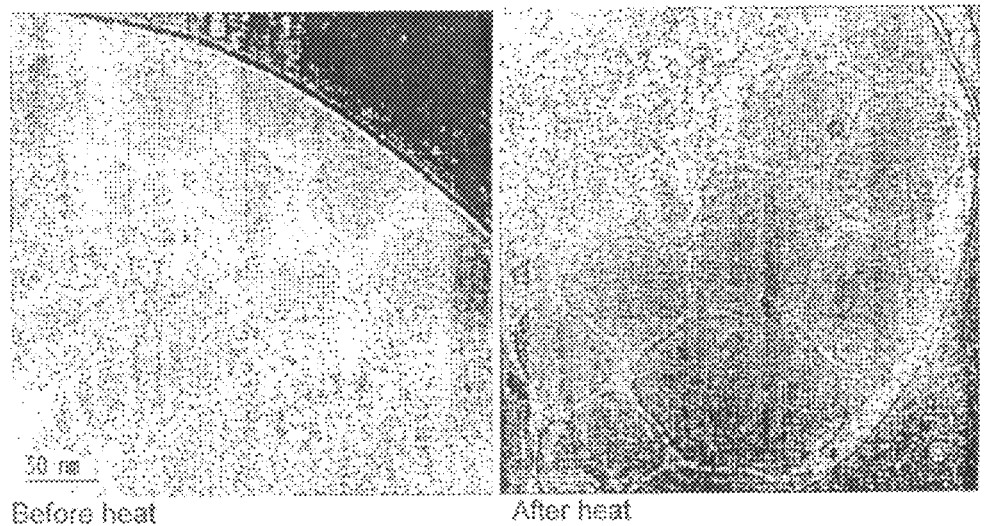
FIG. 13 shows cryo-transmission electron micrographs of a dispersed non-lamellar sample of SPC/GDO/P80 before and after heat treatment.
Figure 14:
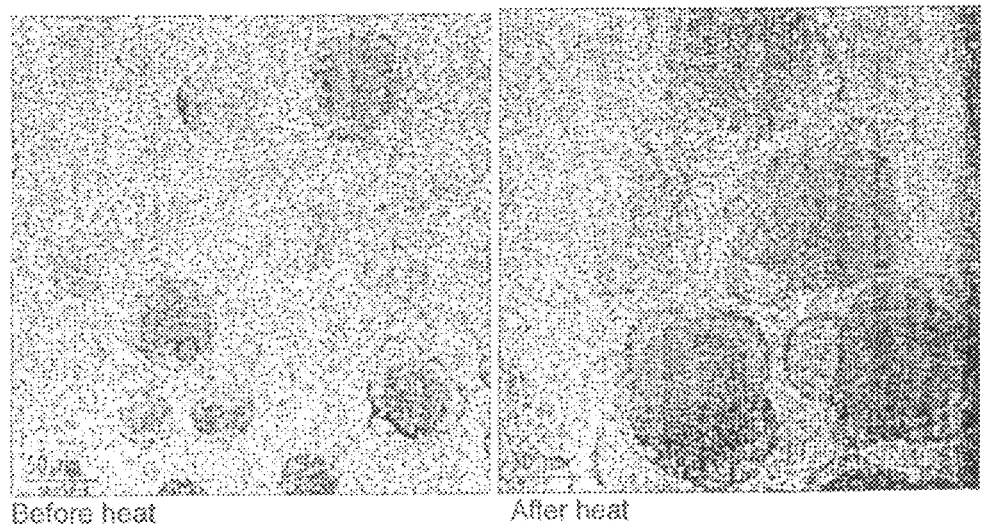
FIG. 14 shows cryo-transmission electron micrographs of a dispersed non-lamellar sample of SPC/GDO/P80 before and after heat treatment.

$^a$PI = polydispersity index, defined as the ratio between the standard deviation of the size distribution and the mean size;
$^b$HT = heat-treatment From the results displayed in the table above, the non-lamellar nanoparticle system is very robust with respect to particle mean size and size distribution upon changes of the SPC/GDO ratio. The heat-treatment can also be observed to narrow the particle size distribution (lower PI) in all cases. Cryo-TEM images of samples #1128 and #1131 before and after heat treatment are shown in FIGS. 13 and 14, respectively, and display non-lamellar particles with a disordered surface structure of multiply connected bilayers enclosing a dense inner non-lamellar core structure.

EXAMPLE 14

Preparation of Liquid Non-Lamellar Particle Precursors

A liquid non-lamellar particle precursor was prepared by mixing SPC (1.45 g), GDO (2.15 g), P80 (0.90 g) and EtOH (0.50 g) followed by end-over-end rotation for 5 h resulting in a homogenous and clear liquid.

A second formulation was prepared by adding 2.0 g of the above liquid formulation to 0.198 g of sterile water followed by vortex mixing for 1 min resulting in a clear and homogenous liquid. The exact composition of the liquid non-lamellar particle precursors are shown in the table below.

Table with compositions of liquid non-lamellar particle precursors

| Sample | Composition (wt %) | Appearance |
|---|---|---|
| Liquid non-lamellar particle precursor 1 | SPC/GDO/P80/EtOH = 29/43/18/10 | Clear, homogenous and light yellow liquid |
| Liquid non-lamellar particle precursor 2 | SPC/GDO/P80/EtOH/H$_2$O = 26.4/39.1/16.4/9.1/9.0 | Clear, homogenous and light yellow liquid |

The liquid precursors were readily dispensed using a syringe with a 27 G needle or sprayed using e.g. a pump-spray device.

EXAMPLE 15

Pharmacokinetics of Octreotide (OCT) Loaded into Liquid Non-Lamellar Particle Precursors after Subcutaneous (s.c.) Injection A liquid non-lamellar particle precursor containing octreotide was prepared as described in Example 15 by mixing SPC, GDO, P80, EtOH and OCT in the proportions indicated in the table below (0.6 mg octreotide per g of formulation). The resulting sample was mixed by end-over-end rotation to yield a clear and homogenous liquid formulation.

Table with composition of non-lamellar particle precursor containing octreotide

| Sample ID | Composition (wt %) SPC/GDO/P80/EtOH/OCT | Appearance |
| --- | --- | --- |
| 2022OCT-C | 28.78/43.17/17.99/10.00/0.06 | Clear, homogenous and light yellow liquid |
| 2022OCT-E | 34.18/51.26/4.50/10.0/0.06 | Clear, homogenous and light yellow liquid |

The liquid non-lamellar particle precursor formulations were injected s.c. in rat at a dose volume of 1 mL/kg corresponding to a dose of 0.6 mg OCT per kg body weight. Blood samples (0.3 mL) were collected pre-dose (one day before dosing), 10 minutes, 30 minutes, 1 hr, 3 hrs, 6 hrs, 24 hrs and 48 hrs after dosing for 2022OCT-C and pre-dose, 1 hr, 6 hrs, 24 hrs, 48 hrs, 120 hrs and 168 hrs after dosing for 2022OCT-E.

The content of OCT in all plasma samples was measured by a competitive immunoassay. Briefly, the OCT peptide coated on a microplate competes for the antibody in solution with the OCT present in the plasma sample. The fraction of antibody remaining in solution is removed, and the fraction bound to the immobilized peptide is quantified, the signal obtained being inversely proportional to the concentration of OCT in the sample.

Figure 15:
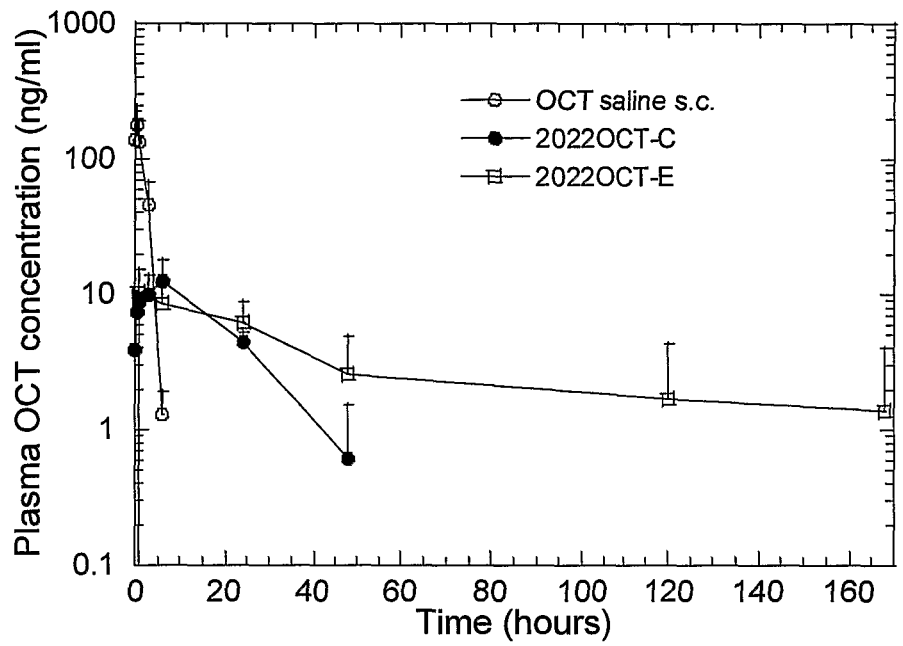
FIG. 15 shows the plasma concentration of Octreotide in rat after subcutaneous administration.

The pharmacokinetics of OCT when formulated in the liquid non-lamellar particle precursors was compared with that of a saline solution of OCT. The results in FIG. 15 show that the non-lamellar particle precursor formulations give low initial plasma levels (low "burst") of OCT ($C_{max}$ decreased by a factor of about 15 compared with the saline case) and a duration of the release (or sustained release) of up to at least 48 h for 2022OCT-C and up to at least 168 hrs (1 week) for 2022OCT-E.

EXAMPLE 16

Pharmacokinetics of OCT Loaded into Non-Lamellar Particles Dispersed in Saline after s.c. Injection A liquid lipid stock solution was prepared by mixing SPC (0.918 g), GDO (1.377 g), P80 (0.405 g) and EtOH (0.30 g) in a glass vial followed by end-over-end rotation for 15 h. OCT (5 mg) was dissolved in sterile water (0.095 g) and 2.2 g of the lipid stock solution was added to the aqueous octreotide solution. The resulting mixture was vortexed until the sample became homogenous. The lipid/octreotide mixture (1.85 g) was added to saline (18.15 g) and the resulting dispersion (0.2 mg OCT/mL) was mixed on a shaking table at 400 rpm for 15 h. The dispersion was thereafter sterilized by sterile filtration (0.22 μm filter). The resulting dispersion was turbid to milky and homogenous with a mean particle size of ca 100 nm as measured by laser diffraction.

The liquid non-lamellar particle precursor formulations were injected s.c. in rat at a dose volume of 3 mL/kg corresponding to a dose of 0.6 mg OCT per kg body weight. Blood samples (0.3 mL) were collected pre-dose (one day before dosing), 10 minutes, 30 minutes, 1 hr, 3 hrs, 6 hrs, 24 hrs and 48 hrs after dosing.

Plasma concentration of OCT was measured as described in Example 16.

Figure 16:
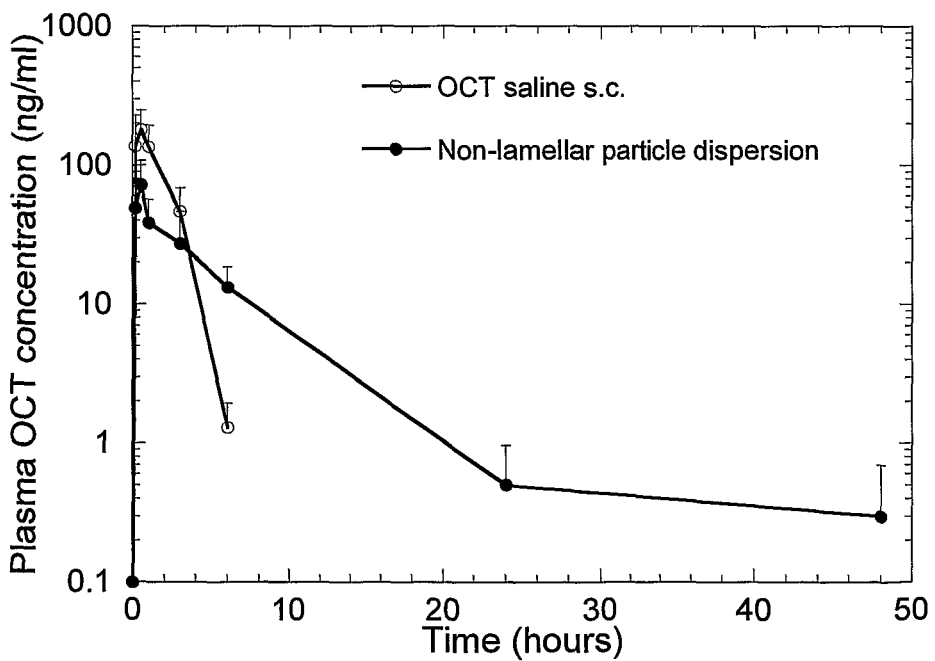
FIG. 16 shows the plasma concentration of Octreotide in rat after subcutaneous administration.

The pharmacokinetics of OCT when formulated in the non-lamellar particles dispersed in saline was compared with that of a saline solution of OCT. The results in FIG. 16 reveal that the non-lamellar particle dispersion gives significantly decreased initial plasma levels of OCT ($C_{max}$ decreased by a factor of about 2.5 compared with the saline case) and a duration of the release (or sustained release) of up to at least 24 h.

EXAMPLE 17

Further Compositions of OCT Loaded into Non-Lamellar Particles for Injection (e.g. Intravenous (i.v.), s.c. or i.m.)

Non-lamellar particle dispersions containing OCT (0.2 mg OCT/mL) was prepared in saline as described in Example 17. The resulting dispersions were turbid to milky and homogenous with a mean particle size of ca 100 nm as measured by laser diffraction. The compositions of the formulations are given in the table below.

Table with compositions of non-lamellar particle dispersions containing OCT

| Sample | Composition (wt %) | Appearance |
| --- | --- | --- |
| 2022OCT-A | SPC/GDO/P80/EtOH/OCT/saline = 2.71/4.06/1.19/0.89/0.02/91.13 | Homogenous and white to light yellow dispersion |
| 2022OCT-B | SPC/GDO/P80/DOPE-PEG(5000)/ EtOH/OCT/saline = 2.47/4.06/1.19/0.24/0.89/0.02/91.13 | Homogenous and white to light yellow dispersion |

The non-lamellar particle dispersions were readily dispensed using a syringe with a 31 G needle or sprayed using e.g. a pump-spray device.

EXAMPLE 18

Formulation of Salmon Calcitonin (sCT) in Liquid Non-Lamellar Particle Precursors Liquid non-lamellar particle precursors containing sCT were prepared as described in Example 14 by mixing SPC, GDO, P80, EtOH and sCT in the proportions indicated in the table below (0.5 mg sCT per g of formulation). The resulting samples were mixed by end-over-end rotation to yield clear and homogenous liquid formulations.

Table with compositions of non-lamellar particle precursors containing sCT

| Sample ID | Composition (wt %) SPC/GDO/P80/EtOH/sCT | Appearance |
|---|---|---|
| 2022sCT-A | 28.78/43.18/17.99/10.00/0.05 | Clear, homogenous and light yellow liquid |
| 2022sCT-B | 30.58/45.88/13.49/10.00/0.05 | Clear, homogenous and light yellow liquid |
| 2022sCT-C | 32.38/48.57/9.00/10.00/0.05 | Clear, homogenous and light yellow liquid |
| 2022sCT-D | 34.18/51.27/4.50/10.00/0.05 | Clear, homogenous and light yellow liquid |

EXAMPLE 19

Freeze-Dried Powder Precursor of Non-Lamellar Particles Containing OCT

A liquid non-lamellar particle precursor was obtained by mixing SPC (0.3046 g), GDO (0.4570 g), P80 (0.1344 g), EtOH (0.100 g) and OCT (0.004 g) followed by end-over-end rotation for 15 h resulting in a clear homogenous liquid. The liquid precursor (0.50 g) containing OCT was added to 9.5 g of sterile water and the resulting dispersion was mixed on a shaking table at 400 rpm for 20 h to yield a homogenous non-lamellar particle dispersion with 0.2 mg OCT/g of formulation. To the non-lamellar particle dispersion (9.0 g) was added 9.0 g of a 1 wt % aqueous solution of CMC and 18 g of a 5 wt % solution of PVP. The resulting mixture was added to a round-bottomed flask and frozen on an EtOH/dry ice mixture followed by freeze-drying overnight. The resulting powder was white to light yellow, of a dry consistency, contained <2 wt % of residual water and the OCT content was 1.3 mg per g of powder. The powder was readily redispersed in saline by vortex mixing to give a milky-white (turbid) non-lamellar particle dispersion.

EXAMPLE 20

Spray-Drying of Non-Lamellar Particles

A spray-dried non-lamellar particle precursor was obtained by mixing 6 g of a pre-made non-lamellar particle dispersion of SPC/GDO/P80 (31/54/15 wt %) (5 wt % amphiphile), prepared as described in Example 1.1, with 12 g of a 1 wt % aqueous solution of CMC and 12 g of a 5 wt % aqueous solution of PVP. The resulting mixture was spray-dried using a BÜCHI Mini Spray Dryer B-290 to give a white to light yellow powder with dry consistency and <2 wt % residual water. The spray-dried powder was readily redispersed in saline by vortex mixing to give a milky-white (turbid) non-lamellar particle dispersion.

EXAMPLE 21

Liquid Non-Lamellar Particle Precursor and Non-Lamellar Particle Dispersion Containing Insulin A liquid lipid stock solution was prepared by mixing SPC (0.918 g), GDO (1.377 g), P80 (0.574 g) and EtOH (0.319 g) in a glass vial followed by end-over-end rotation for 15 h. Insulin (10 mg) was added to sterile water (0.190 g) and 1.80 g of the lipid stock solution was added to the aqueous insulin solution (5 mg insulin per g of formulation). The resulting mixture was vortexed until the sample became homogenous. The lipid/insulin mixture (1.85 g) prepared as described above was added to sterile water (18.15 g) and the resulting dispersion (0.46 mg insulin/mL) was mixed on a shaking table at 400 rpm for 15 h. The resulting dispersion was turbid to milky and homogenous.

EXAMPLE 22

Liquid Non-Lamellar Particle Precursor and Non-Lamellar Particle Dispersion Containing GLP-1

A liquid lipid stock solution was prepared by mixing SPC (0.918 g), GDO (1.377 g), P80 (0.574 g) and EtOH (0.319 g) in a glass vial followed by end-over-end rotation for 15 h. GLP-1 (10 mg) was added to sterile water (0.190 g) and 1.80 g of the lipid stock solution was added to the aqueous insulin solution (5 mg insulin per g of formulation). The resulting mixture was vortexed until the sample became homogenous. The lipid/GLP-1 mixture (1.85 g) prepared as described above was added to sterile water (18.15 g) and the resulting dispersion (0.46 mg GLP-1/mL) was mixed on a shaking table at 400 rpm for 15 h. The resulting dispersion was turbid to milky and homogenous.

The invention claimed is:

1. A particulate composition comprising;
   a) 5 to 50% of at least one phosphatidyl choline component
   b) 5 to 90% of at least one diacyl glycerol component, at least one tocopherol, or mixtures thereof, and
   c) 1 to 40% of at least one non-ionic stabilising amphiphile consisting essentially of surfactants having a molecular weight below 8000 amu, wherein all parts are by weight relative to the sum of the weights of a+b+c and wherein the composition comprises particles of at least one non-lamellar phase structure or forms particles of at least one non-lamellar phase structure when contacted with an aqueous fluid; wherein, when contacted with an aqueous fluid to form particles having a non-lamellar phase structure, no more than 1% of particles have a particle size outside the range of 0.05-1.5 μm; and wherein the compositions are essentially stable in terms of phase behaviour, particle size and particle size distribution for at least 3 months.

2. The composition as claimed in claim 1 wherein component a) comprises at least one PC selected from Egg PC, Heart PC, Brain PC, Liver PC and Soy PC.

3. The composition as claimed in claim 1 wherein component b) comprises a diacyl glycerol having acyl chains with 14 to 18 carbons.

4. A composition as claimed in claim 1 wherein component b) is GDO, or a mixture of tocopherol with GDO.

5. The composition as claimed in claim 1 wherein component a) and/or component b) are derived from a natural source.

6. The composition as claimed in claim 5 wherein component a) has at least 50% C18:1 and/or C18:2 acyl groups and component b) is a diacyl glycerol with at least 50% C18:1 and/or C18:2 acyl groups.

7. The composition as claimed in claim 1 wherein component c) comprises at least one non-ionic stabilising amphiphile selected from are Polysorbates 20 and 80, solutol, d-alpha tocopheryl polyethylene glycol 1000 succinate (Vitamin E TPGS) and polyethoxylated caster oil.

8. The composition as claimed in claim 1 additionally comprising an active agent.

9. The composition as claimed in claim 8 wherein said active agent is at least one selected from octreotide and other somatostatin related peptides, insulin, chlorhexidine digluconate, chlorhexidine dihydrochloride, bisphosphonates, non-steroidal anti-inflammatories, corticosteroids, methotrexate, azathioprine, 6-mercaptopurine and phospholipase inhibitors.

10. The composition as claimed in claim 5 wherein the composition comprises particles of $I_2$ and/or $L_2$ phase structure and/or forms particles of $I_2$ and/or $L_2$ phase structure when contacted with an aqueous fluid.

11. The composition as claimed in claim 1 wherein the average particle size of the particles comprising the composition or formed on contact with an aqueous fluid is 0.1 to 0.6 μm.

12. The composition as claimed in claim 1 further comprising up to 20% of at least one organic solvent having 1 to 6 carbon atoms and/or water-soluble polymers thereof.

13. The composition of claim 1 in the form of:
a) a dispersion
b) a pre-concentrate in a co-solvent, or
c) a dry powder, or a solidified mixture with a biotolerable polymer.

14. A pharmaceutical formulation comprising at least one composition as claimed in claim 5 and at least one biologically tolerable carrier or excipient.

15. The pharmaceutical formulation as claimed in claim 14 in a form selected from suspensions in liquid, powders, tablets, capsules, coated capsules, coated tablets, aerosols, suppositories, drops, creams, transdermal patches and sprays.

16. A formulation as claimed in claim 15, which is suitable for parenteral administration.

17. The composition as claimed in claim 1 wherein the weight ratio of (a):(b) ranges from 1:5 to 3:2.

18. The composition as claimed in claim 1 wherein both PC and DAG components comprise at least 50% oleoyl or linoleoyl acyl groups.

19. A method for the formation of non-lamellar particles comprising forming a mixture comprising;

a) 5 to 90% of at least one phosphatidyl choline component
b) 5 to 90% of at least one diacyl glycerol component, at least one tocopherol, or mixtures thereof, and
c) 2 to 40% of at least one non-ionic stabilising amphiphile consisting essentially of surfactants having a molecular weight below 8000 amu, wherein all parts are by weight relative to the sum of the weights of a+b+c and dispersing said mixture in an aqueous fluid and wherein the composition comprises particles of at least one non-lamellar phase structure or forms particles of at least one non-lamellar phase structure when contacted with an aqueous fluid; wherein, when contacted with an aqueous fluid to form particles having a non-lamellar phase structure, no more than 1% of particles have a particle size outside the range of 0.05-1.5 μm; and wherein the compositions are essentially stable in terms of phase behaviour, particle size and particle size distribution for at least 3 months.

20. A kit for the preparation of a composition in the form of a suspension, said kit comprising at least one particular composition of claim 1 in the form of a powder and optionally instructions for suspending the powder in an aqueous fluid.

21. A method for the treatment of a human or animal subject comprising administration of a composition as claimed in claim 1.

22. The method of treatment as claimed in claim 21 for the treatment of inflammation and/or irritation, in a body cavity.

23. The method as claimed in claim 21 for the treatment of inflammatory bowel disease.

24. A method for the sustained release of an active agent over a period of 1 to 30 days comprising administering a formulation comprising a composition of claim 5 and at least one active agent.

* * * * *